United States Patent
Li et al.

(10) Patent No.: US 10,626,444 B2
(45) Date of Patent: Apr. 21, 2020

(54) METHODS OF ASSAYING NUCLEIC ACIDS OF LOW QUANTITIES USING A BUFFER NUCLEIC ACID

(71) Applicant: ACUDX Inc., Cupertino, CA (US)

(72) Inventors: Xitong Li, Cupertino, CA (US); Zhuanfen Cheng, San Jose, CA (US)

(73) Assignee: Acudx Inc., Cupertino, CA (US)

( * ) Notice: Subject to any disclaimer, the term of this patent is extended or adjusted under 35 U.S.C. 154(b) by 255 days.

(21) Appl. No.: 15/730,608

(22) Filed: Oct. 11, 2017

(65) Prior Publication Data

US 2018/0127808 A1  May 10, 2018

Related U.S. Application Data

(60) Provisional application No. 62/408,624, filed on Oct. 14, 2016.

(51) Int. Cl.
  *C12P 19/34* (2006.01)
  *C12Q 1/6806* (2018.01)
  *C12Q 1/686* (2018.01)

(52) U.S. Cl.
  CPC .......... *C12Q 1/6806* (2013.01); *C12Q 1/686* (2013.01)

(58) Field of Classification Search
  None
  See application file for complete search history.

(56) References Cited

U.S. PATENT DOCUMENTS

| 2009/0170060 A1* | 7/2009 | Kermekchiev | C12Q 1/686 435/2 |
| 2015/0298091 A1* | 10/2015 | Weitz | B01J 19/0046 506/16 |
| 2015/0322501 A1* | 11/2015 | Yaku | C12Q 1/686 435/6.12 |

OTHER PUBLICATIONS

Gawad et al., "Single-cell genome sequencing: Current state of the science", Nature Reviews Genetics, Mar. 2016, pp. 175-188, vol. 17, Macmillan Publishers Limited, New York, NY.

Goodwin et al., "Coming of age: ten years of next-generation sequencing technologies", Nature Reviews Genetics, Jun. 2016, pp. 333-351, vol. 17, Macmillan Publishers Limited, New York, NY.

\* cited by examiner

*Primary Examiner* — Kenneth R Horlick
(74) *Attorney, Agent, or Firm* — Kilpatrick Townsend & Stockton LLP

(57) ABSTRACT

This disclosure provides methods, kits, and compositions to amplify sample DNA of low quantity by adding an amount of buffer DNA before amplification. The method protects the sample DNA against degradation and PCR bias. The method disclosed herein are useful to amplify DNA of low amount, such as genomic DNA from a single cell and therefore are especially useful for genetic diagnostic tests and precision medicine.

13 Claims, 6 Drawing Sheets

Specification includes a Sequence Listing.

METHODS OF ASSAYING NUCLEIC ACIDS OF LOW QUANTITIES USING A BUFFER NUCLEIC ACID

RELATED APPLICATIONS

This application claims the priority benefit of U.S. Provisional Application No. 62/408,624, filed Oct. 14, 2016. The aforementioned priority applications is hereby incorporated herein by reference in entirety for all purposes.

REFERENCE TO A "SEQUENCE LISTING" SUBMITTED AS ASCII TEXT FILES VIA EFS-WEB

The Sequence Listing written in file 101962-000110US-1063461 SequenceListing.txt created on Jan. 22, 2018, 9,378 bytes, machine format IBM-PC, MS-Windows operating system, in accordance with 37 C.F.R. §§ 1.821- to 1.825, is hereby incorporated by reference in its entirety for all purposes.

BACKGROUND OF THE INVENTION

The field of single-cell genomics provides new perspectives to the understanding of genetics by bringing the study of genomes to the cellular level, and opens up new frontiers by dissecting the contributions of individual cells to the biology of ecosystems and organisms. For example, it is now possible to use single-cell genomics to identify and assemble the genomes of unculturable microorganisms (Marcy et al.), evaluate the roles of genetic mosaicism in normal physiology and disease (McConnell et al.), and determine the contributions of intra-tumor genetic heterogeneity in cancer development or treatment response (Wang et al.).

However, this field relies on the study of nucleic acid of very low quantity, such as genomic DNA from a single cell, which requires amplification of the low quantity nucleic acid. Current amplification methods include thermostable DNA polymerase mediated PCR (Troutt et al., Telenius et al.), isothermal DNA polymerase mediated multiple displacement amplification or MDA (Dean et al., Zhang et al. 2001), and hybrid methods such as PicoPLEX (Langmore) and MALBAC (Zong et al.). These methods frequently cause loss of signal from the low quantity of DNA during the amplification due to differences in PCR priming efficiency among sequences, and/or introduction of errors by thermostable polymerases. The errors and biases introduced during these methods, cause problems such as loss of coverage, decreased coverage uniformity, allelic imbalance, allelic dropout, and errors affecting detection of single nucleotide variation and measurement of copy number variation especially during single cell genome or exome amplification. See de Bourcy et al., Gawad et al., Hou et al., Huang et al.

SUMMARY OF INVENTION

The present disclosure provides methods, compositions, and kits useful for analysis of nucleic acids.

In one aspect, this disclosure provides a method of treating a sample DNA comprising the steps of: combining the sample DNA with a buffer DNA to produce a total assay DNA for a reaction, wherein the buffer DNA is distinct from the sample DNA, wherein the mass ratio of the buffer DNA to the sample DNA in the total assay DNA is at least 5, wherein the amount of the sample DNA is no higher than a threshold.

In another aspect, this disclosure provides a method of treating a biological sample for DNA analysis, wherein the biological sample comprise a sample DNA that is in an amount of no more than a threshold, the method comprising combining the biological sample with a buffer DNA, and extracting a total assay DNA comprising at least a portion of the sample DNA and at least a portion of the buffer DNA for a reaction, wherein the mass ratio of buffer DNA to sample DNA in the total assay DNA is at least 5.

In some embodiments, the threshold of the sample nucleic acid in the total assay nucleic acid is 100 pg or less. In some embodiments, the biological sample is a single cell. In some embodiments, the method further comprises amplifying the sample DNA. In some embodiments, the method of claim 1 or 2, wherein the amount of total assay DNA in the reaction is 50 pg or greater.

In some embodiments, the buffer DNA contains at least one rare cleavage site. In some embodiments, the rare cleavage site comprises at least six base pairs and is recognized by a restriction endonuclease. In some embodiments, the restriction endonuclease is selected from the group consisting of NotI, SfiI, PmeI, PacI, and AscI.

In some embodiments, the sample DNA is from a single cell without amplification. In some embodiments, the sample DNA is from not more than 2 cells, 5 cells, 10 cells, 50 cells, or 100 cells.

In another aspect, this disclosure provides a method for amplifying a sample DNA in a reaction comprising the steps of: (a) mixing the sample DNA with a buffer DNA to form a total assay DNA in the reaction, wherein the amount of the sample DNA is no higher than a threshold, wherein the mass ratio of the buffer DNA to the sample DNA is at least 10; and (b) simultaneously amplifying the sample DNA and buffer DNA to produce amplified sample DNA and amplified buffer DNA.

In some embodiments, the method further comprises sequencing the amplified sample DNA and amplified buffer DNA. In some embodiments, each molecule of the buffer DNA comprises at least one rare cleavage site per 200 base pairs on the average, and the rare cleavage site is recognizable by a enzyme. In some embodiments, the enzyme is a restriction endonuclease.

In some embodiments, the method further comprises the steps of: treating the amplified sample DNA and amplified buffer DNA with the enzyme, wherein the enzyme cuts each buffer DNA molecule into two or more fragments; and separating the amplified sample DNA from fragments of amplified buffer DNA. In some embodiments, the method further comprises ligating one or more adaptors to the buffer DNA and sample DNA before amplification.

In some embodiments, the buffer DNA used in the method comprises at least one rare cleavage site per molecule and the method further comprises: treating the amplified sample DNA and amplified buffer DNA with an enzyme, wherein the enzyme binds to the rare cleavage site and cut each buffer DNA molecule into two or more fragments, and performing a second round of amplification of the amplified sample DNA and buffer DNA fragments, wherein the second round of amplification is performed by extending primers that bind to the adaptors in the amplified sample DNA.

In another aspect, this disclosure provides a method of amplifying a sample RNA comprising the steps of: converting the sample RNA into a sample cDNA, mixing a buffer DNA with the sample cDNA to form a total assay DNA; and amplifying the total assay DNA. In another aspect, this disclosure provides a method of amplifying a sample RNA comprising the steps of: mixing a buffer RNA with the sample RNA to form a total assay RNA, converting the total assay RNA into a total assay DNA, wherein the total assay DNA consists of sample cDNA converted from sample RNA and buffer cDNA converted from buffer cDNA, and amplifying the total assay DNA.

In some embodiments, the sample RNA used in the method above is from a single cell without amplification. In some embodiments, the method further comprises ligating one or more adaptors to the sample DNA and buffer DNA before amplification, and wherein the amplification is performed by extending primers binding to the one or more adaptors. In some embodiments, the buffer DNA or the buffer cDNA comprises at least one rare cleavage site recognizable by an enzyme, wherein the method further comprises: treating the amplified total assay DNA with the enzyme, which upon binding to the rare cleavage site, cuts the buffer DNA into fragments, and further amplifying the total assay DNA from (e) by using primers binding to the adaptors.

In another aspect, this disclosure provides a kit for treating a sample DNA comprising: (a) a buffer DNA, wherein the buffer DNA is at least 40 bp, and in an amount that when mixed with the sample DNA, the mass ratio of the buffer DNA and the sample DNA is at least 10, wherein each molecule of the buffer DNA comprises at least one or more rare cleavage sites, and (b) instruction for mixing buffer DNA and a sample DNA. In some embodiments, the kit further comprises a polymerase, one or more primers for amplifying the sample DNA. In some embodiments, the kit additionally comprises one or more adaptors and a ligase for ligating the adaptors to the sample DNA and buffer DNA.

In another aspect, this disclosure provides a composition comprising a total assay DNA. The total assay DNA comprises a sample DNA and a buffer DNA and the buffer DNA is distinct from the sample DNA. The mass ratio of buffer DNA molecules to the sample DNA molecules in the total assay DNA is at least 10. In some embodiments, the amount of sample DNA is less than a threshold. In some embodiments, the buffer DNA is at least 40 base pairs, and wherein each buffer DNA molecule comprises at least one rare cleavage sites. In some embodiments, the composition further comprises one or more adaptors and one or more primers that can bind to the one or more adaptors.

In any of the above embodiments or aspects, the sample DNA can be equivalent to 100,000× or less, 10,000× or less, 5000× or less, 1000× or less, 100× or less, 50× or less, 32× or less, 16× or less, 8× or less, 4× or less, 2× or less, or 1× coverage of human genome.

BRIEF DESCRIPTION OF THE DRAWINGS

The present application includes the following figures. The figures are intended to illustrate certain embodiments and/or features of the invention, and to supplement any description(s) of the invention, and not to limit the scope of the invention.

DETAILED DESCRIPTION OF THE INVENTION

1. Introduction

Figure 1:
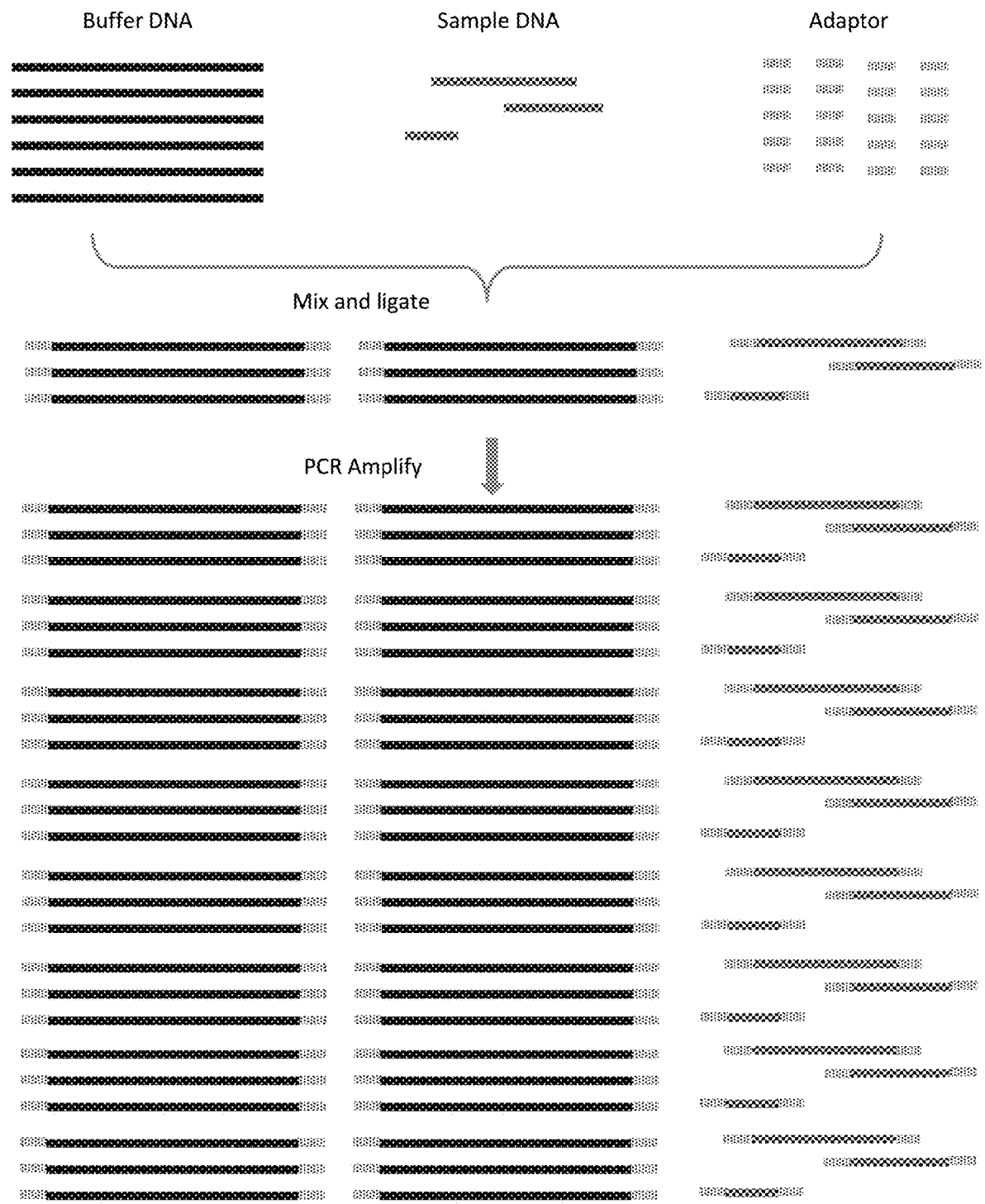
FIG. 1 is an illustration of an embodiment of the invention showing combining buffer DNA and sample DNA, ligating with adaptors, and amplifying the buffer DNA and sample DNA by PCR.

Provided herein are methods for amplification of sample DNA of low quantity. According to these methods an amount of buffer DNA is combined with the sample DNA before amplification. Without intending to be bound by a specific mechanism, the method protects the sample DNA against degradation and PCR bias so that the amplified sample DNA more likely to represent the original sample DNA in proportion as compared to method not using the buffer DNA. The methods disclosed herein may be used to amplify very small quantities of sample DNA, such as genomic DNA from a single cell, and therefore are especially useful for genetic diagnostic tests and precision medicine.

2. Definitions

In this disclosure and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Although any methods, devices and materials similar or equivalent to those described herein can be used in the practice or testing of the invention, the preferred methods, devices and materials are now described. All publications mentioned herein are incorporated herein by reference for the purpose of describing and disclosing the invention components that are described in the publications that might be used in connection with the presently described invention.

As used herein, the term "distinct" refers to the fact that two sequences are different and the difference can be readily detected by methods well known in the art, e.g., sequencing, hybridization or amplification.

As used herein, the term "cDNA" refers to a double-stranded DNA synthesized from a single stranded RNA template in a reaction catalyzed by a reverse transcriptase. The term "sample cDNA" refers to the cDNA produced using a single stranded sample RNA as a template. The term "buffer cDNA" refers to the cDNA produced using a single stranded buffer RNA as a template.

As used herein, depending on context, the term "a buffer nucleic acid", "a sample nucleic acid" refer to the type of nucleic acid as well as a population of molecules of buffer nucleic acid molecules and sample nucleic acid molecules. For example, a sample DNA also refers to a population of sample DNA molecules, and a sample cDNA refers to a population of cDNA molecules produced using a single stranded sample RNA as a template.

As used herein, the term "total assay nucleic acid" refers to the pool of the sample nucleic acid molecules and the total buffer nucleic acid molecules in a reaction. Depending on the context, a total assay DNA can be a tool of sample DNA and buffer DNA molecules, a pool of sample cDNA and buffer cDNA molecules, or a pool of a sample cDNA and buffer DNA molecules in a reaction.

As used herein, the term "mass ratio" refers to the ratio of the total mass of buffer nucleic acid molecules to the total mass amount of sample nucleic acid molecules in the total assay nucleic acid. The units of mass used in this disclosure include but are not limited to the submultiples for gram (or g) the values, symbols (used interchangeably as name), names of which are listed in table 1.

TABLE 1

Submultiples for gram (g)

| Value | Symbol | Name |
| --- | --- | --- |
| $10^{-3}$ g | mg | milligram |
| $10^{-6}$ g | μg | microgram |
| $10^{-9}$ g | ng | nanogram |
| $10^{-12}$ g | pg | picogram |
| $10^{-15}$ g | fg | femtogram |
| $10^{-18}$ g | ag | attogram |

As used herein, the terms "amplification" refers to amplifying a nucleic acid, e.g., sample DNA/cDNA, or a portion thereof, for at least 2, at least 3, at least 4, at least 5, at least 6, at least 10, at least 15, at least 20, at least 30, or at least 40 cycles, e.g., 6-10 cycles, 12-35 cycles, 20-40 cycles, 10-30 cycles, or amplifying a nucleic acid or a portion thereof such that the amount of the nucleic acid or a portion thereof is increased to an amount that is at least 2, 4, 8, 16, or 32 times of the amount of the nucleic acid or the portion thereof before the amplification.

3. Embodiments 3.1. Biological Samples

The present disclosure provides methods and kits for nucleic acid analysis of a biological sample. The sample can be from any organism of interest, or a population of such organism of interest. The sample can be from human or non-human species. Biological samples suitable for use in the present invention can include, but are not limited to, samples of bodily fluids samples of bodily fluids (including, but not limited to, blood, urine, serum, lymph, saliva, anal and vaginal secretions, perspiration and semen); cells; tissue; biological warfare agent samples; research samples (e.g., products of nucleic acid amplification reactions, such as PCR amplification reactions); purified samples, such as purified genomic DNA; RNA preparations; bacteria; and viruses. In some embodiments, the sample is a single cell. In some embodiments, the single cell is a single diploid mammalian cell, a single insect cell, a single yeast cell, or a single bacterial cell, or a single virus. In some embodiments, the sample is no more than two (2) cells, no more than three (3) cells, no more than four (4) cells, no more than 10 cells, no more than 50 cells, or no more than 100 cells. The cells can be one or more prokaryotic cells or eukaryotic cells. In some embodiments, the sample is a droplet of blood or serum from an individual and has a volume of no more than 500 microliters, no more than 100 microliters, no more than 50 microliters, no more than 30 microliters, no more than 20 microliters, no more than 15 microliters, or no more than 10 microliters.

3.2. Sample Nucleic Acid

The present invention can be used to amplify and assay a sample nucleic acid. The sample nucleic acid can be a DNA, a RNA, or a mixture thereof. A sample nucleic acid can be from any material. In some embodiments, the sample nucleic acid is a low quantity nucleic acid ("LQNA"). The small amount of nucleic acid in a LQNA is so low, i.e. no higher than a threshold, that amplification is required before assaying or characterizing the nucleic acid. For example, the amount of LQNA, if it is DNA, is no higher than are 100 picogram (pg), 50 pg, 20 pg, 10 pg, 5 pg, 2 pg, 1 pg, 100 femtogram (fg), 50 fg, 20 fg, 10 fg, 1 fg, 100 attogram (ag), or 10 ag; The amount of LQNA, if it is RNA, is no higher than 50 pg, 25 pg, 10 pg, 5 pg, 2 pg, 1 pg, 0.5 pg, 50 fg, 20 fg, 10 fg, 5 fg, 0.5 fg, 50 ag, or 5 ag. In some embodiments, the LQNA is double-stranded nucleic acid. In some embodiments, the LQNA is single-stranded nucleic acid. In some embodiments, the LQNA is RNA isolated from a single cell. In some embodiments, the LQNA is DNA produced by converting the RNA from a single cell or a single RNA virus through reverse transcription.

In some embodiments, the sample nucleic acid is a homogenous population of nucleic acid molecules, e.g., having identical sequences. In some embodiments, the sample nucleic acid is a heterogeneous population of nucleic acid molecules, i.e., having different lengths, and/or sequences. In some embodiments, the sample nucleic acid is derived from different types of tissues or from different individuals.

The nucleic acid molecules of the sample nucleic acid can have various lengths. In some embodiments, the average length of the nucleic acid molecules of the sample DNA is at least 40 base pairs (bp), at least 100 bp, at least 200 bp, or at least 1000 bp. In some embodiments, the sample nucleic acid is a sample RNA and has the average length of at least 40 nucleotides, at least 100 nucleotides, at least 200 nucleotides, or at least 1,000 nucleotides.

In some embodiments, prior to amplification steps, the sample RNA is converted into sample cDNA through reverse transcription using methods well known in the art.

In some embodiments, the sample DNA is obtained from a biological sample, as described above. Methods for preparing sample nucleic acid from a biological sample are well known in the art. See, e.g., Sambrook et al., Molecular Cloning: A Laboratory Manual (1999); Ausubel et al., eds., Current Protocols in Molecular Biology, (John Wiley and Sons, Inc., NY, 1999), or the like. Commercial kits are also readily available for this purposes, such as PureLink™ Genomic DNA Mini Kit by Thermo Fisher, MagMAX™ FFPE DNA/RNA Ultra Kit by Thermo Fisher, REPLI-g Single Cell DNA Library Kit by Qiagen, and REPLI-g Single Cell RNA Library Kit by Qiagen. In some embodiments, the sample DNA exists in an unextracted state or unpurified state, i.e., the sample DNA remains inside the nucleus and associated with histone proteins in a biological sample.

3.3. Buffer Nucleic Acid

Disclosed herein is a method of treating a biological sample comprising a sample nucleic acid, or a sample nucleic acid obtained from a sample by combining it with a buffer nucleic acid before the sample nucleic acid is amplified. In preferred embodiments, the sample nucleic acid is a LANA. Without intending to be bound by a specific mechanism, the buffer nucleic acid can protect the LANA from the damaging factors frequently present in the amplification reactions that causes DNA fragment loss, mutations and chimaeras and/or the introduction of artefacts, such as amplification bias. Examples of damaging factors include but are not limited to endogenous or contaminating nuclease (e.g. DNase and/or RNase), radicals, radiation, and any chemical or biomolecule that breaks or modifies nucleic acid, which are intentionally or unintentionally introduced to the reaction.

The buffer nucleic acid as disclosed herein is used in an amount sufficient to render the amount of total assay nucleic acid to be an amount ranging from 1 pg to 1000 ng or more. For example the amount can be at least 50 pg, at least 100 pg, at least 200 pg, at least 500 pg, at least 1 ng, at least 2 ng, at least 5 ng, or at least 10 ng. In some embodiments, the mass ratio between the buffer nucleic acid and the sample nucleic acid ranges from 2 to 1,000,000,000 or more. For example the mass ratio can be at least 10, at least 20, at least 50, at least 100, at least 1,000, at least 10,000, at least 100,000, or at least 1,000,000.

In some embodiments, the buffer nucleic acid disclosed herein comprises a homogenous population of nucleic acid molecules, e.g., having identical sequences and lengths. In some embodiments, the buffer nucleic acid comprises a heterogeneous population of nucleic acid molecules, i.e., having different lengths, and/or sequences. The buffer nucleic acid molecules can be of any length. In some embodiments, the buffer nucleic acid is a buffer DNA and has an average length of at least 40 base pairs (bp), at least 100 bp, at least 200 bp, or at least 1000 bp.

In some embodiments, the buffer nucleic acid comprises one or more modified nucleotides that contain modifications to the base, sugar, and/or phosphate moieties.

In some embodiments, the average length of the buffer nucleic acid molecules can be shorter than that of the sample nucleic acid molecules, for example, the ratio between the two is no higher than 1, no higher than 0.8, no higher than 0.5, no higher than 0.2, or no higher than 0.01. In some embodiments, the average length of the buffer nucleic acid molecules can be longer than that of the sample nucleic acid molecules, for example, the ratio between the two is at least 2, at least 5, or at least 10.

A buffer nucleic acid disclosed herein is distinct from the sample nucleic acid to be combined with. In some embodiments, the buffer nucleic acid is derived from a species that is different from the sample nucleic acid. In some embodiments the buffer nucleic acid is synthetic. In some embodiments, the buffer nucleic acid comprises barcode sequences that are not present in the sample nucleic acid so that multiple amplifications can be pooled together and differentiated through the barcode sequences. In some embodiments, the buffer nucleic acid comprises endonuclease recognition sites, e.g. rare cleavage sites, see below. In some embodiments, the size of buffer nucleic acid is distinct from sample nucleic acid.

3.4. Rare Cleavage Sites

In some embodiments, the buffer DNA or the buffer cDNA, converted from buffer RNA, comprises a rare cleavage ("RC") site that can be recognized by restriction enzyme. In some embodiments, the rare cleavage site comprises at least six (6) base pairs. In some embodiments, the rare cleavage site comprises eight (8) base pairs. In some embodiments, the restriction enzyme is selected from the group consisting of NotI, SfiI, PmeI, PacI, and AscI. In some embodiments, the rare cleavage site is not present in the sample DNA or the sample cDNA. In some embodiments, the number of rare cleavage site in the sample DNA is no more than a maximum number per 1000 bp sequence on average wherein the said maximum number is 1, 0.1, 0.01, 0.001, 0.0001, or less than 0.0001. In some embodiments, the buffer DNA/cDNA molecules comprise one rare cleavage site. In some embodiments, the buffer DNA or buffer cDNA molecules comprise on the average at least 1 rare cleavage site for every 500 bp, every 400 bp, every 300 bp, every 200 bp, every 170 bp, every 150 bp, every 100 bp, every 80 bp, every 70 bp, every 50 bp, every 30 bp, or every 20 bp. In some embodiments, the rare cleavage sites are distributed evenly on the buffer DNA or buffer cDNA. In some embodiments, the rare cleavage sites are randomly distributed on the buffer DNA or buffer cDNA. In some embodiments, the buffer DNA or cDNA comprise the same rare cleavage site. In some embodiments, the buffer DNA or cDNA comprises two or more different rare cleavage site. The restriction enzyme, upon binding to the rare cleavage site, can cut the buffer DNA or buffer cDNA into fragments.

3.5. Producing Buffer Nucleic Acid

The buffer nucleic acid is not bound by a specific production method and can be prepared by a variety of methods. Methods for preparing buffer nucleic acid include but are not limited to chemical synthesis of DNA, extraction of plasmid DNA from cultured bacteria or yeasts, extraction of certain DNA from tissues, extraction of DNA from cultured cells, extraction of DNA from bacteria, yeasts, virus or virus culture. Buffer DNA can also be prepared by PCR DNA amplification, multiple displacement of amplification, rolling cycle amplification, reverse transcription, in vitro DNA polymerase reaction, etc. Buffer RNA can also be prepared by in vitro transcription, etc.

In some embodiments, both the sample nucleic acid and the buffer nucleic acid are double stranded DNA. In some embodiments, both the sample nucleic acid and the buffer nucleic acid are RNA and they are combined and converted into double stranded DNAs by reverse transcription. In some embodiments, the sample nucleic acid is RNA, which is converted into double stranded DNA through reverse transcription and then combined with double stranded buffer DNA.

3.6. Adaptors

In some embodiments, the methods disclosed herein comprise ligating adaptors to sample nucleic acid and buffer nucleic acid. An adaptor refers to a DNA sequence that may be appended to (e.g. ligated to) DNA molecules, e.g., sample DNA or sample cDNA, buffer DNA or cDNA. Adaptors typically comprise primer binding sequences, and thus once added to the population of sample molecules, primers specific to the adaptor can be used to detect, amplify and/or sequence the sample or buffer DNA/cDNA. Adaptor sequences are typically not present in the sample nucleic acid sequences. In some embodiments, the adaptor also includes one or more additional features such as, restriction endonuclease recognition sites, polymerase recognition sequences, and/or primer binding sequences.

Primer binding sequences in adaptors will be of sufficient length to allow hybridization of a primer, with the precise length and sequence dependent on the intended functions of the primer (e.g., extension primer, indexing sequence, etc.). In some embodiments, primer binding sequences are at least 8, at least 10, at least 12, at least 15 or at least 18 bases in length.

Adaptors may have a length, structure, and other properties appropriate for a particular analysis platform and intended use. For example, adaptors may be single-stranded, double-stranded, or partially-double stranded, and may be of a length suitable for the intended use. For example, adaptors may have length in the range of 10-200 nucleotides, 20-100 nucleotides, 40-100 nucleotides, or 50-80 nucleotides. In some embodiments, an adaptor may comprise one or more modified nucleotides that contain modifications to the base, sugar, and/or phosphate moieties.

In some embodiments, only one adaptor is ligated to a molecule of the sample nucleic acid or buffer nucleic acid. In some embodiments, two adaptors are used, one ligated to the 5' end and the other ligated to the 3' end of a molecule of the sample or buffer nucleic acid. In some embodiments, the two adaptors ligated to the same molecule of sample or buffer DNA or buffer cDNA have identical sequence. In some embodiments, the two adaptors have different sequences. The adaptors can be ligated into a DNA molecule using methods well known in the art. Most commonly the ligating the adaptors to the sample DNA/cDNA or buffer DNA/cDNA is mediated through a DNA ligase, such as a T4 DNA ligase. In some embodiments, the adaptors comprise a non-human sequence.

3.7. Methods 3.7.1. Combining Buffer Nucleic Acid with a Sample Nucleic Acid to Form Total Assay Nucleic Acid This disclosure teaches methods of combining buffer nucleic acid with a sample nucleic acid to form total assay nucleic acid prior to amplifications documented in present and prior arts as illustrated in FIG. 1. The combining process can be a direct combination meaning that a buffer nucleic acid is directly combined with sample nucleic acid, or an indirect combination meaning that a buffer nucleic acid is combined with a biological sample comprising a sample nucleic acid. In an indirect combination process, a DNA extraction step is used. Both processes are described below.

3.7.1.1. Indirect Combination: Combining Buffer Nucleic Acid with a Biological Sample Comprising a Sample Nucleic Acid In some embodiments, a biological sample, e.g., a single cell, is combined with a buffer nucleic acid as described above, and the biological sample comprises a sample nucleic acid. In some embodiments, the biological sample comprises a sample nucleic acid in an unextracted state before being combined with a buffer nucleic acid. The sample nucleic acid along with the buffer nucleic acid combined into the biological sample are then extracted to form a total assay nucleic acid including the buffer nucleic acid that is already present before the extraction.

3.7.1.2. Direct Combination: Combining Buffer Nucleic Acid Directly with a Sample Nucleic Acid In some embodiments, the sample nucleic acid, extracted from the biological sample, are combined directly with buffer nucleic acid to form total assay nucleic acid.

3.7.1.3. Combination Devices

In some cases, the total assay nucleic acid is formed in a microwell plate. In some cases, the total assay nucleic acid is formed in microdroplets or in microfluidic devices. Microfluidic devices and devices for producing microdroplets are commercially available, for example, from Advanced Liquid Logic, Morrisville, N.C., and RainDance Technologies, Lexington, Mass.

3.7.2. Ligating Adaptors to Sample DNA/cDNA and Buffer DNA/cDNA

Figure 2:
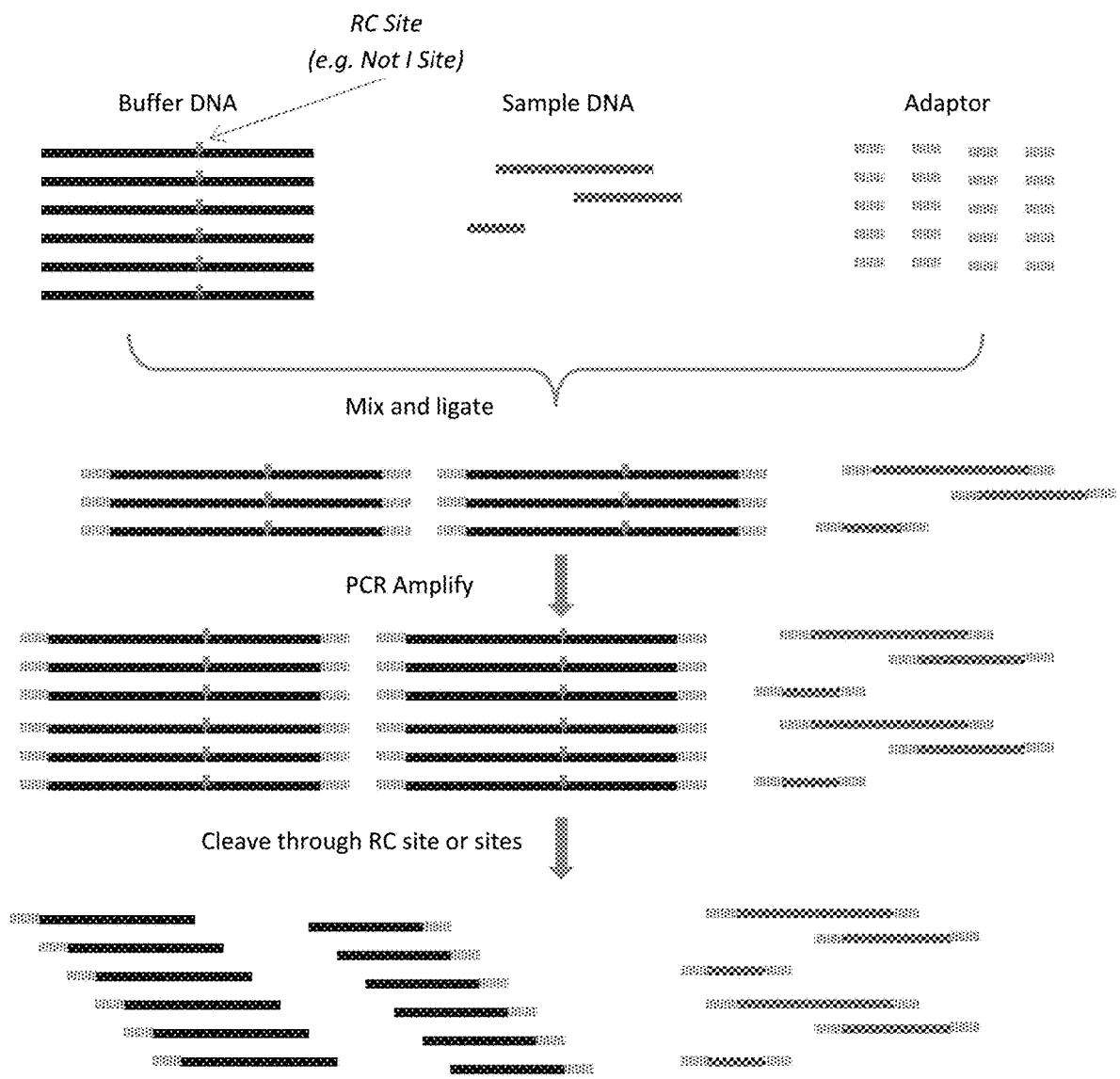
FIG. 2 is an illustration of an embodiment of the invention showing buffer DNA, and sample DNA with adaptors. The buffer DNA in this embodiment of the invention comprises rare cleavage sites. After PCR amplification, the amplified buffer DNA is cut into fragments through enzyme digestion at the locations of the rare cleavage sites.
Figure 3:
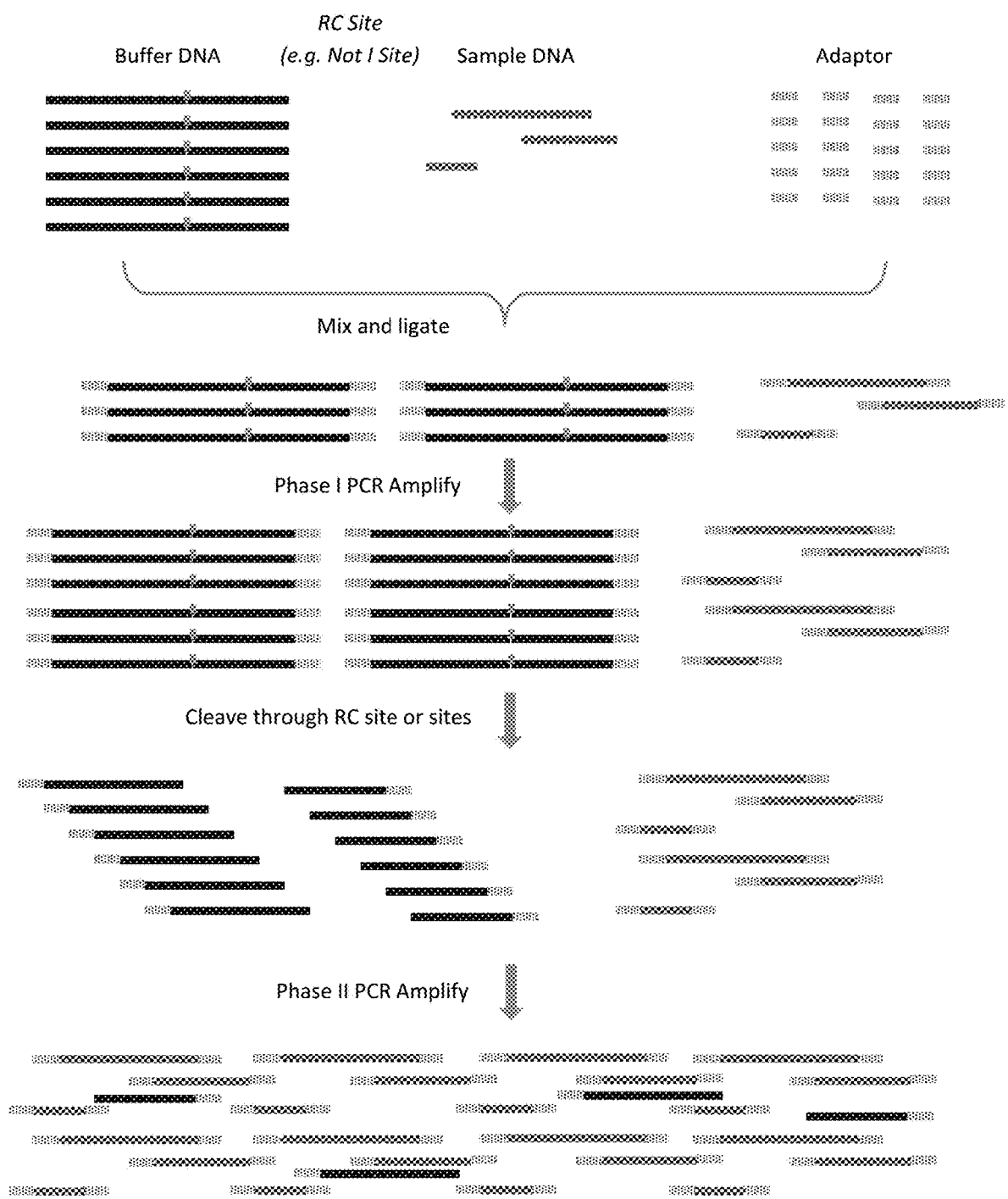
FIG. 3 is an illustration of an embodiment of the invention showing separating buffer DNA from sample DNA after restriction enzyme digestion and enriching sample DNA by performing a second phase amplification.

In some embodiments, the sample DNA/cDNA and buffer DNA/cDNA are ligated to one or more adaptors by a DNA ligase. In some embodiments, adaptors are ligated to the two ends of a sample DNA/cDNA molecule and the two ends of a buffer DNA/cDNA molecule (FIGS. 1, 2, and 3). In some embodiments, these adaptors can be used to bind to primers to amplify the sample DNA/cDNA and buffer DNA/cDNA.

3.7.3. Amplification

Figure 4:
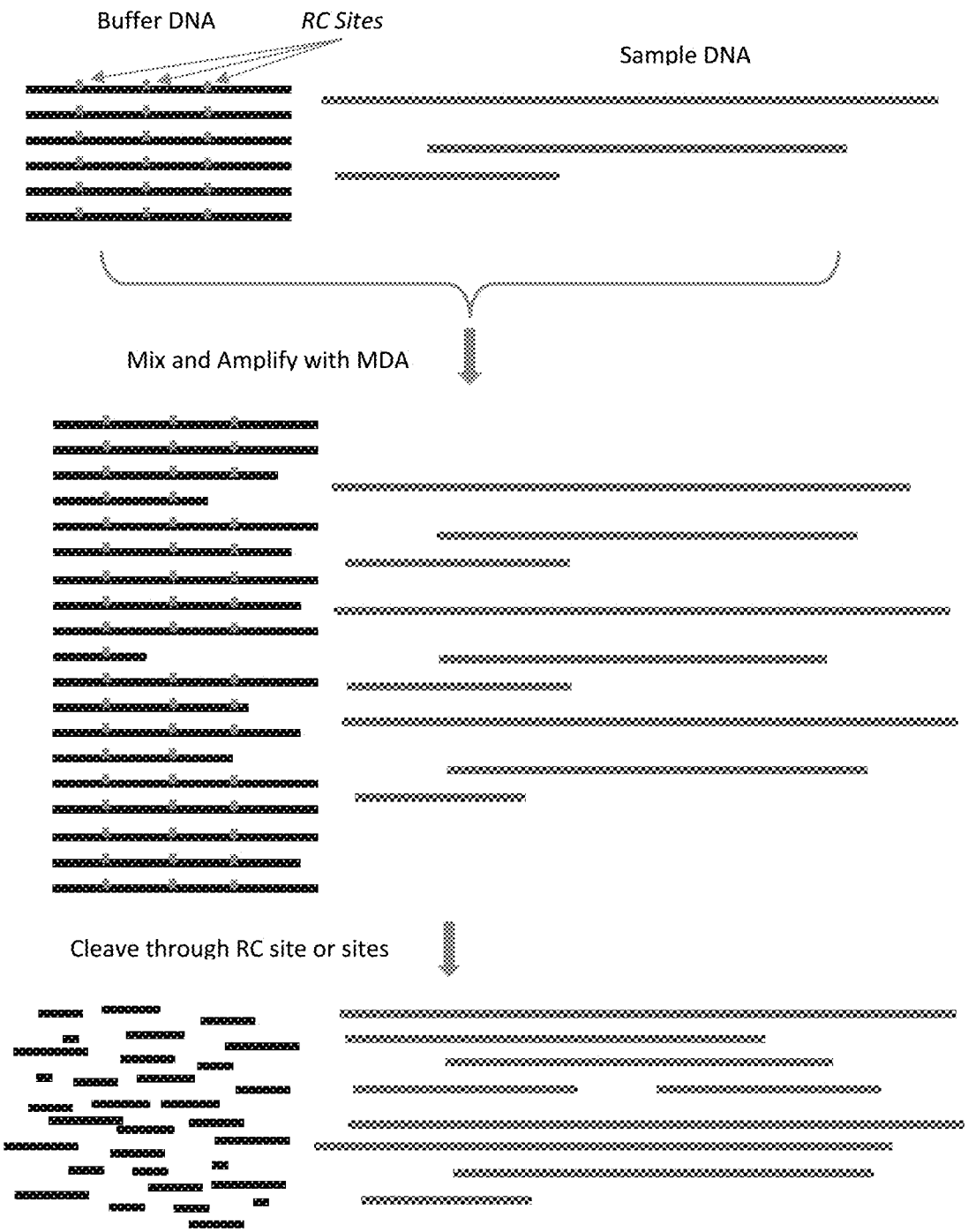
FIG. 4 is an illustration of an embodiment of the invention showing buffer DNA and sample DNA are amplified through amplification, for example, the multiple displacement amplification (MDA) method followed by enzymatic digestion at rare cleavage sites.

In some embodiments, the sample DNA/cDNA the buffer DNA/cDNA are amplified using a DNA polymerase. Any DNA amplification methods can be used for this invention. Amplification methods are well known and are substantially described in, for example, Gawad et al and Mahmud et al. In one embodiment, amplification involves extending primers that are bound to the adaptors in the sample DNA and buffer DNA molecules, see FIGS. 1 and 2 (one phase PCR) or FIG. 3 (two phase PCR). In one embodiment, the amplification involves hybridizing random PCR primers to the sample nucleic acid and buffer nucleic acid followed by PCR cycles of amplification (DOP-PCR) using random PCR primers. In one embodiment, the DOP-PCR is performed using a thermostable DNA polymerase. Non-limiting examples of the thermostable DNA polymerases include Taq polymerase and Pfu polymerase. In another embodiment, the amplification involves multiple displacement amplification ("MDA") using an isothermal DNA polymerase. In some embodiments, the isothermal DNA polymerase has strand displacement activity. Non-limiting example of isothermal DNA polymerases that are suitable for use in the invention include Phi29 polymerase, Bst DNA polymerase, and deepVentR DNA polymerase. In another embodiment, the amplification uses limited isothermal amplification and followed by PCR amplification of the amplicons generated during the isothermal step, e.g., the PicoPLEX method (Langmore) and MALBAC (Zong et al). In another embodiment, the sample DNA and or buffer DNA are circularized and amplified using rolling circle amplification ("RCA"). FIG. 4 is an illustration of an embodiment of the invention showing buffer DNA and sample DNA are amplified through multiple displacement amplification (MDA) method followed digestion at rare cleavage sites. In this particular example, each buffer DNA molecule comprises multiple RC sites that rarely occur in sample DNA. After enzymatic digestion at rare cleavage site, these buffer DNA molecules were fragmented into pieces that are significantly smaller than sample DNA and thus can be separated from sample DNA through gel electrophoresis or DNA purification column.

The amplified sample DNA/cDNA and amplified buffer DNA/cDNA can then be analyzed according to intended purposes, using assay platforms including but not limited to sequencing, QPCR, digital PCR, and/or microarray analysis.

FIG. 1 illustrates some embodiments of the methods described in 3.7.1-3.7.3. FIG. 1 shows that buffer DNA and sample DNA are mixed. Sample DNA and buffer DNA molecules are ligated with adaptors at both the 5' and 3' ends. The ligation and mixing of the sample and buffer DNA can be performed simultaneously and can also sequentially, not limited to any particular order. The buffer DNA and sample DNA are then amplified by PCR. The buffer DNA shown in FIG. 1 is a homogenous population of molecules and the sample DNA is a heterogeneous population of molecules.

3.7.4. Selection and/or Enrichment of Sample DNA after Amplification

In some embodiments, a selection and/or enrichment of sample DNA is performed in order to reduce the representation of the buffer DNA/cDNA in the total assay DNA before characterization of the sample DNA (described below). In some embodiments, amplified sample DNA/cDNA from the buffer DNA/cDNA are separated from the sample DNA/cDNA. In some cases, the separation involves fragmenting the amplified buffer DNA/cDNA at rare cleavage sites by one or more restriction endonucleases. The fragmentation produces buffer DNA/cDNA fragments having properties distinct from the sample DNA fragments such that the fragments can be separated from the amplified sample DNA/cDNA. In some embodiments, the distinct property is size differentiation.

In these embodiments, the rare cleavage sites are present in the buffer DNA at a high frequency, see above, such that buffer DNA are cut into fragments of significantly smaller in size than the sample DNA. These buffer DNA fragments can then be separated from the sample DNA. Methods that can be used to separate the nucleic acids based on size distinction are well known, for example, separation using size selection column or gel electrophoresis. In some embodiments, fragmentation of the buffer DNA by endonuclease causes buffer DNA fragments missing one or both primer binding sites that are required for amplification. A second phase of amplification can be performed after fragmentation. During the second phase amplification, the sample DNA is further amplified while the buffer DNA cannot, thereby enriching the sample DNA. In some embodiments, the second phase of amplification is performed using the same primers as the first phase of amplification, i.e., the amplification performed before fragmentation. In a particular embodiment, the sample DNA/cDNA molecules are ligated with adaptors at both ends and the primers used for the amplification bind to these adaptors. FIG. 3 illustrates an embodiment of the invention in which enrichment is performed. As shown in FIG. 3, sample DNA with adaptors comprising primer binding sites ligated to both 5' and 3' ends and is amplified during the second phase amplification while buffer DNA is not amplified. The second phase amplification result in buffer DNA diminished and sample DNA enriched in the total assay DNA. These selection and/or enrichment steps enhance the detection of interested features in the sample nucleic acid.

FIG. 2 illustrates some embodiments of the method steps as described in 3.7.4. The buffer DNA used in this particular embodiment contains a rare cleavage site ("RC"), for example, Not I site. Buffer DNA and sample DNA are mixed and ligated with adaptors at both 5' and 3' ends. A PCR amplification is performed using two primers that bind to the adaptors to amplify both the buffer DNA and sample DNA. Upon the completion of the PCR amplification, a restriction endonuclease is added to the reaction, which cleaves the each molecule of the buffer DNA into two fragments.

FIG. 3 illustrates additional embodiments of the method steps as described in 3.7.4. FIG. 3 shows in addition to the steps shown in FIG. 2, after a first phase of PCR amplification followed by restriction endonuclease digestion, a second phase of PCR amplification is performed using a primer pair that also bind to the adaptors that are at the 5' and 3' ends of each molecule of the sample DNA. Buffer DNA are not amplified because each molecule of the buffer DNA fragments produced by the digestion contains only one adaptor and thus one of the primer pair cannot bind to each of the buffer DNA fragment.

FIG. 4 illustrates some embodiments of the method steps as described in 3.7.4. In these embodiments, each of the buffer DNA molecules comprises rare cleave site at a high frequency, for example on the average at least one rare cleavage site for every 500 bp, every 400 bp, every 300 bp, every 200 bp, every 170 bp, every 150 bp, every 100 bp, every 80 bp, every 70 bp, every 50 bp, every 30 bp, or every 20 bp. Buffer DNA and sample DNA are mixed and amplified using any method that is well known in the art. Upon completion of the amplification, a restriction endonuclease is added to the reaction, which cleave the buffer DNA into fragments at the location where the rare cleave sites are present. This results buffer DNA being cut into small fragments which can be readily separated from sample DNA using e.g., electrophoresis methods or size exclusion columns.

3.7.5. Analysis of Sample DNA

In some embodiments, the amplified sample DNA/cDNA and the amplified and enriched sample DNA/cDNA are analyzed by sequencing. Sequence information for buffer DNA/cDNA from the sequence information for sample DNA/cDNA can be sorted based on the distinct sequence features in the buffer DNA. In some embodiments, sequencing the amplified sample DNA/cDNA and buffer DNA/cDNA is by hybridizing and extending a sequencing primer to the adaptor that has been ligated to the sample DNA or sample cDNA molecules. In some embodiments, the sequencing primer hybridizes to a known sequence within the sample DNA or cDNA and is extended to generate sequence information.

Any suitable sequence determination method may be used to determine the sequence of the amplified sample DNA/cDNA and amplified buffer DNA/cDNA, for example, sequencing-by-synthesis, pyrosequencing, sequencing by ligation, and others. Methods for performing these sequencing reactions are well known, for example, as reviewed and described in Ronaghi et al., Hodkinson and Grice, Goodwin et al., the relevant disclosures are herein incorporated by reference.

3.8. Kits

Also provided herein are kits for carrying out some embodiments of the invention. In one embodiment, the kit comprises a buffer DNA as described above and an instruction for combining buffer DNA and a sample DNA. In some embodiments, the kit further comprises one or more components selected from the group consisting of a polymerase, one or more DNA and/or RNA oligos, and a buffer for amplifying the sample DNA and buffer DNA. Non-limiting examples of polymerases are Phi29 polymerase, Taq polymerase, pfu polymerase, Bst DNA polymerase, and deep-VentR DNA polymerase. In some embodiments, the kit further comprises one or more adaptors and a ligase that can be used to ligate the one or more adaptors to the sample and buffer DNA molecules.

3.9. Compositions

Also provided herein are compositions comprising a total assay DNA, wherein the total assay DNA comprises a sample DNA and a buffer DNA. The buffer DNA is distinct from the sample DNA, and the mass ratio of buffer DNA molecules to the sample DNA molecules is at least 10. In some embodiments, the buffer DNA is at least 40 base pairs, and wherein each buffer DNA molecule comprises at least one rare cleavage sites. In some embodiments, the composition further comprises one or more adaptors as disclosed above and one or more primers that can bind to the one or more adaptors. In some embodiments, the sample DNA is equivalent to 100,000× or less, 10,000× or less, 5000× or less, 1000× or less, 100× or less, 50× or less, 32× or less, 16× or less, 8× or less, 4× or less, 2× or less, or 1× coverage of human genome.

4. Applications

The methods disclosed are especially useful in applications in which the nucleic acid sample that needs to be detected is of a low quantity. These include, but are not limited to, a number of diagnostic applications, such as sequencing and assembling new microbial genomes, identifying genetic mosaicism in multicellular organisms, detecting copy number variation ("CNV") and single nucleotide variation ("SNV") from tissue, single cell DNA sequencing, single cell RNA sequencing, and single cell DNA methylome sequencing.

5. Embodiments

Embodiment 1

A method of treating a sample DNA comprising the steps of: combining the sample DNA with a buffer DNA to produce a total assay DNA, wherein the buffer DNA is distinct from the sample DNA, wherein the mass ratio of the buffer DNA to the sample DNA in the total assay DNA is at least 5, wherein the amount of the sample DNA is no higher than a threshold.

Embodiment 2

A method of treating a biological sample for DNA analysis, wherein the biological sample comprises a sample DNA that is in an amount of no more than a threshold, the method comprising
combining the biological sample with a buffer DNA, and
extracting a total assay DNA comprising at least a portion of the sample DNA and at least a portion of the buffer DNA, wherein the mass ratio of buffer DNA to sample DNA in the total assay DNA is at least 5.

Embodiment 3

The method of embodiment 2, wherein the biological sample is a single cell.

Embodiment 4

The method of embodiment 1 or 2, further comprising amplifying the sample DNA.

Embodiment 5

The method of embodiment 1 or 2, wherein the threshold is 100 pg or less.

Embodiment 6

The method of embodiment 1 or 2, wherein the amount of total assay DNA is 50 pg or greater.

Embodiment 7

The method of embodiment 1 or 2, wherein the buffer DNA contains at least one rare cleavage site.

Embodiment 8

The method of embodiment 7, wherein the rare cleavage site comprises at least six base pairs and is recognized by a restriction endonuclease.

Embodiment 9

The method of embodiment 8, wherein the restriction endonuclease is selected from the group consisting of NotI, SfiI, PmeI, PacI, and AscI.

Embodiment 10

The method of embodiment 1, wherein the sample DNA is from a single cell.

Embodiment 11

The method of embodiment 1, wherein the sample DNA is from not more than 2 cells, 5 cells, 10 cells, 50 cells, or 100 cells.

Embodiment 12

A method for amplifying a sample DNA comprising the steps of:
a. mixing the sample DNA with a buffer DNA to form a total assay DNA,
wherein the amount of the sample DNA is no higher than a threshold,
wherein the mass ratio of the buffer DNA to the sample DNA is at least 10, and
b. amplifying the sample DNA and buffer DNA to produce amplified sample DNA and amplified buffer DNA.

Embodiment 13

The method of embodiment 12, wherein the method further comprises sequencing the amplified sample DNA and amplified buffer DNA.

Embodiment 14

The method of embodiment 13, wherein the method further comprises sequencing the amplified buffer DNA.

Embodiment 15

The method of embodiment 12, wherein each molecule of the buffer DNA comprises at least one rare cleavage site per 200 base pairs on the average, wherein the rare cleavage site is recognizable by a restriction endonuclease.

Embodiment 16

The method of embodiment 15, further comprising the steps of:
a. treating the amplified sample DNA and amplified buffer DNA with the enzyme, wherein the enzyme cuts each buffer DNA molecule into two or more fragments, and b. separating the amplified sample DNA from fragments of amplified buffer DNA.

Embodiment 17

The method of embodiment 15, wherein the sample DNA is derived from a single cell.

Embodiment 18

A method of embodiment 12, wherein the step (a) of the method further comprises ligating one or more adaptors to the buffer DNA and sample DNA.

Embodiment 19

The method of embodiment 18, wherein the buffer DNA comprises at least one rare cleavage site per molecule and wherein the method further comprises:
treating the amplified sample DNA and amplified buffer DNA with an enzyme, wherein the enzyme binds to the rare cleavage site and cut each buffer DNA molecule into two or more fragments, and
performing a second round of amplification of the amplified sample DNA and buffer DNA fragments, wherein the second round of amplification is performed by extending primers that bind to the adaptors in the amplified sample DNA.

Embodiment 20

The method of amplifying a sample RNA comprising the steps of:
a. converting the sample RNA into a sample cDNA,
b. mixing a buffer DNA with the sample cDNA to form a total assay DNA;
c. amplifying the total assay DNA.

Embodiment 21

The method of amplifying a sample RNA comprising the steps of:
a. mixing a buffer RNA with the sample RNA to form a total assay RNA,
b. converting the total assay RNA into a total assay DNA, wherein the total assay DNA consists of sample cDNA converted from sample RNA and buffer cDNA converted from buffer cDNA, and
c amplifying the total assay DNA.

Embodiment 22

The method of embodiment 20 or 21, wherein the sample RNA is from a single cell without amplification.

Embodiment 23

The method of embodiment 20 or 21, wherein the method further comprises ligating one or more adaptors to the sample DNA and buffer DNA before amplification, and wherein the amplification is performed by extending primers binding to the one or more adaptors.

Embodiment 24

The method of embodiment 20 or 21, wherein the buffer DNA or the buffer cDNA comprises at least one rare cleavage site recognizable by an enzyme, wherein the method further comprises:

d. treating the amplified total assay DNA with the enzyme, which upon binding to the rare cleavage site, cuts the buffer DNA into fragments, and
e. further amplifying the total assay DNA from (e) by using primers binding to the adaptors.

Embodiment 25

A kit for treating a sample DNA comprising:
a. a buffer DNA,
wherein the buffer DNA is at least 40 bp, and in an amount that when mixed with the sample DNA, the mass ratio of the buffer DNA and the sample DNA is at least 10,
wherein each molecule of the buffer DNA comprises at least one or more rare cleavage sites, and
b instruction for mixing buffer DNA and a sample DNA.

Embodiment 26

The kit of embodiment 20, further comprise a polymerase, one or more primers for amplifying the sample DNA.

Embodiment 27

The kit of embodiment 21, wherein the kit further comprises adaptors and a ligase for ligating the adaptors to the sample DNA and buffer DNA.

Embodiment 28

A composition comprising a total assay DNA, wherein the total assay DNA comprises a sample DNA and a buffer DNA,
wherein the buffer DNA is distinct from the sample DNA, and the mass ratio of buffer DNA molecules to the sample DNA molecules is at least 10,
wherein the amount of sample DNA is less than a 10 ng, and
wherein the buffer DNA is at least 40 base pairs, and wherein each buffer DNA molecule comprises at least one rare cleavage sites.

Embodiment 29

The composition of embodiment 28, wherein the composition further comprises one or more adaptors and one or more primers that can bind to the one or more adaptors.

6. Examples

It is to be understood that this invention is not limited to the particular devices, machines, materials and methods described. Although particular embodiments are described, equivalent embodiments may be used to practice the invention.

The invention, now being generally described, will be more readily understood by reference to the following examples, which are included merely for purposes of illustration of certain aspects and embodiments of the present invention and are not intended to limit the invention.

The claimed methods are hereinafter generally referred to as C-level protected amplification (CPAD)

6.1. Test 1. Protection and Amplification of Sample DNA Containing Trace Amount of Seven Spike DNAs Using CPAD.

Figure 5:
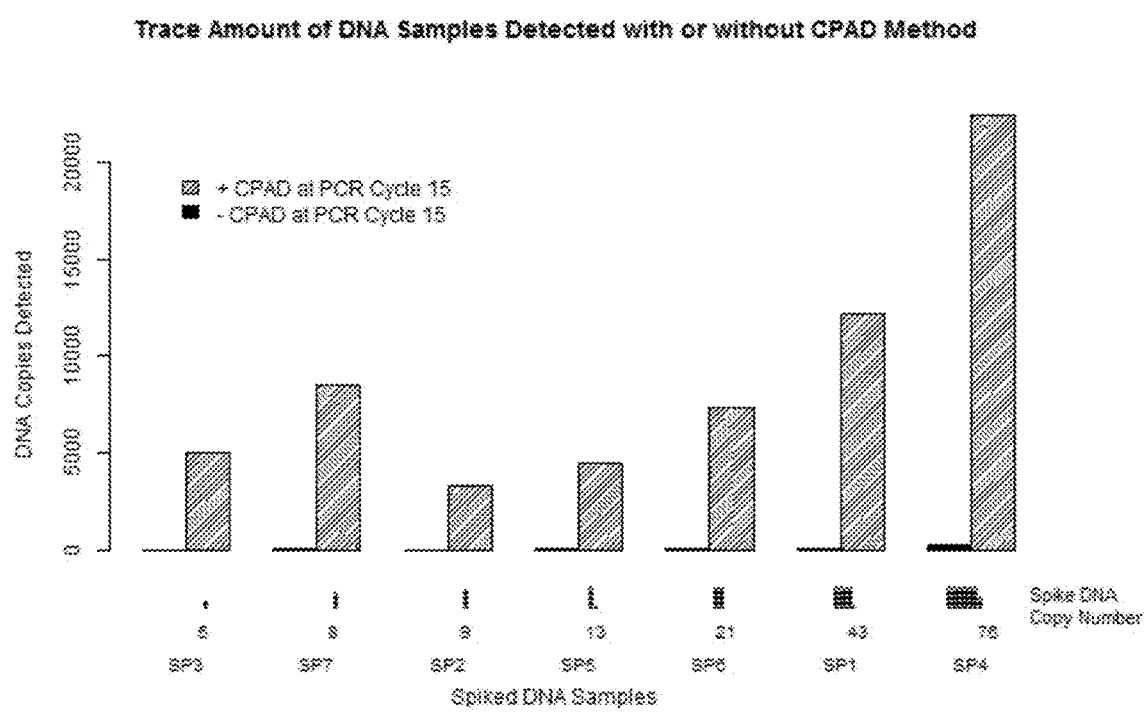
FIG. 5 is an illustration of an embodiment of the invention showing copies of sample DNAs detected with or without the claimed method.

In order to test CPAD performance for protection and amplification, a sample DNA was prepared by mixing together seven DNA fragments called spike DNAs and labeled as SP1, SP2, SP3, SP4, SP5, SP6, and SP7. The spike DNAs have sequences distinct from human genome (FIG. 5) and are of various lengths ranging from 297 to 504 nucleotide base pairs (Table 2). The mass quantities of SP1, SP2, SP3, SP4, SP5, SP6, and SP7 DNAs mixed in the sample are 20, 5, 2.5, 40, 5, 10, and 2.5 attogram respectively, which correspond to 43, 9, 5, 76, 13, 21, and 8 molecular copies respectively (see table 2). The resulting mixture has a total 85 attogram of spike DNAs, a quantity far less than a the total amount of genomic DNA in a typical single cell—e.g., typically, a diploid human cell has genomic DNA amount in the order of magnitude of 6 picogram, a yeast cell contains genomic DNA in the order of magnitude of 12 femtogram, and a E. coli bacterium contains genomic DNA in the order of magnitude of 5 femtogram.

A buffer DNA of linear double stranded DNA of size 2961 base pairs (SEQ ID NO: 8) was prepared and 5 nanogram of which was used for the test. The buffer DNA sequence is distinct from all seven spike DNA sequences in that no common sequence greater than any continuous 15 nucleotides exists between the buffer DNA and each spike DNA. There is one NotI restriction enzyme site present at nucleotide position 986.

In order to test the protection effect of CPAD method, one microliter of human blood plasma solution was artificially introduced as the damaging factor.

Two parallel reactions labeled as #1 and #2 were set up. Reaction #1 was performed using the CPAD method (shown as "+CPAD" in FIG. 4 and FIG. 5; as "CPAD" in Table 2). Reaction #2 was performed without the CPAD method (shown as "CPAD" in FIG. 4 and FIG. 5; as "Control" in Table 2). Test 1 was performed according to the protocol described below.

6.2. Test 1 Protocol

I. DNA Preparation.

Two Reactions are prepared: #1 was performed using the CPAD method (+CPAD) and #2 was performed without the CPAD method (−CPAD). The reaction mixtures in #1 and #2 are prepared according to the following table:

| Reagents | #1 | #2 |
| --- | --- | --- |
| 1 ng/μl buffer DNA | 1.5 μl | 0 μl |
| 10 mM TrisCl pH 8 | 0 μl | 1.5 μl |
| 20 mg/ml Protease K | 1.0 μl | 1.0 μl |
| Sample DNA (85 ag/4 μl in 10 mM Tris Cl) | 4.0 μl | 4.0 μl |

One drop of blood (12 μl) was collected into a clean tube with 50 μl of 10 mM EDTA in 1×PBS and mixed immediately and centrifuged at 300 g for 2 min at 4° C. The supernatant was taken out and split into two aliquots of 21.5 μl each and mixed into the solutions of tube #1 and #2 as prepared above. Additional 1.2 μl of 5% SDS was added and mixed into each tube, then the two tubes were incubated at 60° C. for 30 min. The DNA from each tube was then purified using NEB's spin column (New England Biolabs, T10305) and eluted out in 26 μl 10 mM TrisCl pH8.

NEBNext UltraII End Prep Enzyme mix (1.5 μl) and Reaction buffer (3.5 μl) were added to the tube #1 and #2 containing 25 μl elution of the DNA prepared. The two reaction tubes were then taken to a thermocycler with lid temperature to ≥75° C. went through 30 minutes of incubation at 20° C., 30 minutes of incubation at 65° C., and were held at 4° C. until the next adaptor ligation steps.

For the tubes #1 and #2, The adaptor ligation started with mixing 1.25 μl of NEBNext Adaptor for Illumina (diluted to 0.6 μM), NEBNext UltraII End Prep Reaction Mix (30.0 μl), NEBNext UltraII Ligation Master Mix (15.0 μl), and NEBNext UltraII Ligation Enhancer (0.5 up. The reactions then went through an incubation at 20° C. for 15 min. User Enzyme (1.5 μl, from NEB's primer kit E7335) was added to each tube and the reactions were incubated at 37° C. for 15 min with heated lid set to ≥47° C.

The tubes #1 and #2 containing the adaptor-ligated DNA from above steps went through a purification using SPRI beads. A volume of 58 μl of SPRI beads (1.2 fold in volume) was added to each tube. The tubes were incubated at room temperature for 5 minutes and placed on a magnetic stand to separate the beads from solution (about 5 minutes). The supernatants were discarded and the beads were washed with 80% ethanol before air-dried at room temperature. Then the DNA from each tube were eluted out with 30 μl of 10 mM TrisCl pH8. Aliquots of 14 μl purified DNA solutions were transferred to fresh tubes again labelled #1 and #2 for PCR amplification.

Q5 Master Mix (NEB), enzyme (Taq Core Kit, Qiagen), buffer (Taq Core Kit, Qiagen), Index Primers, and Universal Primers were added to each tube according to Q5 Master Mix instruction for PCR amplification. Phase I PCR went through 6 cycles. Then 0.5 μl of NotI was added to each of PCR reactions for incubation at 37° C. for 10 min. The reactions then continued into Phase II PCR for 9 more cycles. The Phase I PCR, NotI digestion, and Phase II PCR program is specified in Table 3 below.

TABLE 3

PCR program for Phase I and Phase II PCR in test 1.

| Cycle step | Temp (° C.) | Time | # of cycles |
| --- | --- | --- | --- |
| Initial Denaturation | 98 | 30 sec | 1 |
| Denaturation | 98 | 10 sec | 6 |
| Annealing/Extension | 65 | 70 sec | |
| Add NotI* | 37 | 10 min | 1 |
| Denaturation | 98 | 10 sec | 9 |
| Annealing/Extension | 65 | 60 sec | |
| Final Extension | 65 | 5 min | 1 |
| Hold | 4 | ∞ | |

Figure 6:
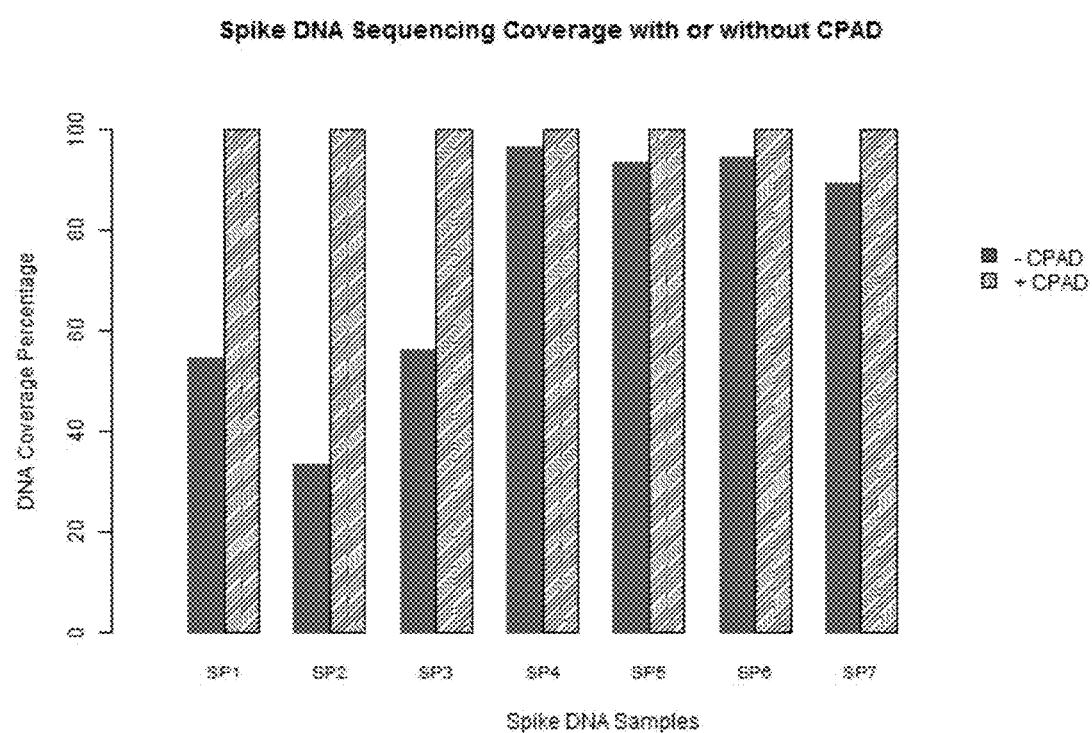
FIG. 6 shows the results of sequencing coverage of spike DNAs with or without the claimed method.

After Phase II PCR, SPRI beads were used to purify the DNA from tubes #1 and #2. The amplified and purified DNA products of the two reactions were then sequenced. Results shows using the CPAD method, the sample DNA were well protected as shown by sequencing coverage percentage. The sample DNA was also well amplified as measured by nucleotide coverage and copies detected. In contrast, the control shows no significant amplification of sample DNA (Table 2, FIG. 5, and FIG. 6).

TABLE 2

| SEQ ID NO | Spike DNA | Length (Nt) | Mass Spiked (ag) | Copies Spiked | CPAD | | | Control | | |
|---|---|---|---|---|---|---|---|---|---|---|
| | | | | | Nt Sequenced | Copies Estimated | Coverage | Nt Sequenced | Copies Estimated | Coverage |
| 1 | Sp1 | 439 | 20 | 43 | 1833395 | 12223 | 100% | 12221 | 81 | 54.4% |
| 2 | Sp2 | 504 | 5 | 9 | 495716 | 3305 | 100% | 760 | 5 | 33.3% |
| 3 | Sp3 | 497 | 2.5 | 5 | 753692 | 5025 | 100% | 3794 | 25 | 56.3% |
| 4 | Sp4 | 492 | 40 | 76 | 3365724 | 22438 | 100% | 43576 | 291 | 96.5% |
| 5 | Sp5 | 365 | 5 | 13 | 669385 | 4463 | 100% | 6611 | 44 | 93.4% |
| 6 | Sp6 | 449 | 10 | 21 | 1103707 | 7358 | 100% | 7776 | 52 | 94.7% |
| 7 | Sp7 | 297 | 2.5 | 8 | 1277670 | 8518 | 100% | 15137 | 101 | 89.2% |

REFERENCES de Bourcy, C. F. et al. PLoS ONE 9(8): e105585 (2014).
Dean, F. B., et al. Genome Res. 11:1095-1099 (2001).
Gawad, C. et al. Nature Reviews Genetics 17:175-188 (2016).
Goodwin, S. et al. Nature Reviews Genetics 17, 333-351 (2016).
Hodkinson, B. P. and Grice E. A. Adv Wound Care (New Rochelle) 4(1): 50-58 (2015).
Hou, Y. et al. Gigascience 4:37 (2015).
Huang, L., et al. Annu. Rev. Genomics Hum. Genet. 16:79-102 (2015).
Langmore, J. P. Rubicon Genomics, Inc. Pharmacogenomics 3:557-560 (2002).
Marcy, Y. et al. Proc. Natl Acad. Sci. USA 104:11889-11894 (2007).
McConnell, M. J. et al. Science 342:632-637 (2013).
Mahmud et al., International Journal of Scientific Research and Education, 3:9 (2015).
Ronaghi et al. Anal. Biochem. 242: 84-89 (1996)
Troutt, A. B., et al. Proc. Natl Acad. Sci. USA 89:9823-9825 (1992).
Telenius, H. et al. Genomics 13:718-725 (1992).
Wang, Y. et al. Nature 512:155-160 (2014).
Zhang, D. Y., et al. Mol. Diagn. 6:141-150 (2001).
Zong, C., et al. Science 338:1622-1626 (2012).

Table of illustrative sequences DNA sequences of seven spike DNAs mixed to form a testing sample DNA SEQ ID NO: 1: SP1
GAATATTCTGTGTCCTGGGATATCACTTCCCGCCGGAACAGCTTGTGATT
GGACAACCACAGAACCAGCACTGTGGAGGGGAAGTGTCGCCCCGCAGCTA
CACAGGCTTGTGCCTAACTCCTGTCTTTTCTTTTTCCCAGGGAGGAAGAG
ACAGCCGCTCTGGATCTCCCATGGCGAGACGCTGAGAGCCCTCCCCGCTC
AGCCTTCCCGAATCCTGCCCTCGGCTTCTTAATATAACTGCCTTAAACTT
TTAATTCTACTTGCACCGATTAGCTAGTTAGAGCAGACCCTCTCTTAATC
CCGTGGAGCCGTGATCGCGGTGGGGCCAGGCCCACGGCACCCCGACTGGT
TAAAACTATTCGTCCCTTTTCGTTTGAAGATTGAGTTTTCTCGGGGTCTT
CTCAGCCCTGACTTGTTCCCCGTGCACCTTGTTCGACTC SEQ ID NO: 2: SP2
TGACTTGTTCCCCGTGCACCTTGTTCGACTCCGGAGGTTCAGGTGCACGG
ACACCCTTCCAAGTTCACCCCTACTCCATCCTCAGACTTTTCACGGTGAG
GCACACCCCTCCAGCTTCCGTGGGCACTGCGGATAGACAGGCACACCGCC
AAGGAGCCAGAGAGCATGGCGCAGGGGACTGTGTGGTCCAGGCTTCCTTT
GTTTTCTTCCCCCTAAAGAGCTTTGTTTTTCCTAACAGGATCAGACAGTC
TTGGAGTGGCTTATACAACGGGGGCTTGTGGTATGTGAGCACAGGCTGGG
CAGCTGTGAGAGTCCAGAGTGGGGTGGCCCTGGGGACACTTCCAGGCCAG
CTATCCCCTGCACCCCACCAGCTGATTTCGAGCGTGGCAGAGGGAAGGAA
AGGGGCGAGTGGGCTGGGCAATGGCCCCAACAGGAAACGGGGACTTAGGA
GAACACGCTGGAGATATGTGTGGCCGCCAAATGTCACCATCTCTCCTCAG
TGGC Table of illustrative sequences DNA sequences of seven spike DNAs mixed to form a testing sample DNA SEQ ID NO: 3: SP3
AACAGGAAACGGGGACTTAGGAGAACACGCTGGAGATATGTGTGGCCGCC
AAATGTCACCATCTCTCCTCAGTGGCTCCCCAGAGCTGGTGCTTTTAAGA
ACCCTGTTTCCTCTCAGAGCCCAGGGAGAGTCCAAGGACATGGCGCATCT
GGAAGTGGGACTGCAGGAGTTCTCTGGTGGCCTCGTGCTGTCCCTCTGGC
CACTTCTCATGGTGGGGTGGTCAGCGGCAGCTCGCCATGGCAGTGCCCAT
TGGTACACACTAACCTCGGTGGAAAAATAACCATTCCCTGCCTCCTAGAA
AGGACTCATTCTTAGCTTTAGGGGGGTTCCTGTCACTGAATCGAGTCGCT
GCCCTGGATGCAGGGCTGGCCTGGGCGACGCTCCAGGGATGAGGAGCTGA
GAACCCCAGTCTAATAATGTCCATCGACACCTCCTTATCCCTCTAACGTA
CTATGTCTTTTGATTTAGCATGCCTTCTGTAGACCTTCCAAAGAGCC SEQ ID NO: 4: SP4
AAAACCCTCCAGATTGTCCCACGGGAGTGTTTGCCCTCCAGTGTGACTGA
ACGACCTTGCCCATGGCTTCGTCCAGACAGCGCAGCTGCAGTATGGCTGG
ACAGAAGCACCTACTATTCTTGAATATTGAAATAAAATAATAAACTTGCA
ATGATCTTTGCCCAGGTGTCTCATTTTGCACGGCAGCCTGTAGGCGTGAG
CCCGAGTGAAGCACAGCCTCGTCGCAGGGTGGAGGGCTCTTCCTCAGGGG
CACCGGGTTGCTTCACGGTGCCCTTGGGAGAATACCTCAAGGGGCACGTT
GAGGAGGCCATGCATTGATAAATCAAGAAGATGGAGTAGAGGTGATGTGG
GACAGTGACCCACAACACACAAGGAAAAGGATTTTCAGTCACTCTGAGGA
CACTTTTCAAAGCCATTGTCCTAGGAAACACTGCAGAAAAGCGGGTCACG
CGCTTTATCCACGGCGGACGGGGATTAAGTGAAGCATTCTTC SEQ ID NO: 5 SP5
GAACGCTGCGCCTCTGGGATCTCACAACGCAAGTAGCTGCTTTGGAATCT
TGGGGGGAAAGTGGGCAGAACTGAGGTAGATTCGCCGGGGTGCAGTCTCC
CCTTGGTAATTGGTCCTTTTGTAGAGGGTAAAGCAACATTTGGGGGTGTT
GTTTTAAACTGGGTACCTATGAAGTGTCTCATCTTGTACGTTGTCTTAGA
TGGGCATTTGGCAGATGTAATAGAGGATCCTAGTGATGACAAGACGACAT
TGTCAACCAATCCCCCACAAGGGAATGAGGACATGTCCTGCAATTCTGAA
TGGGTTCTCTGATACATGTCAGACATGACATAGGCTAGTAGTAGGTTCTA
AGCCACGTGTGGACT SEQ ID NO: 6: SP6
GAACGCTGCGCCTCTGGGATCTCACAACGCAAGTAGCTGCTTTGGAATCT
TGGGGGGAAAGTGGGCAGAACTGAGGTAGAATTCCTGCAGCCCAATTCCG
ATCATATTCAATAACCCTTAATATAACTTCGTATAATGTATGCTATACGA
AGTTATTAGGTCCCTCGAGGGGATCACAGTCTCCCCTTGGTAATTGGTCC
TTTTGTAGAGGGTAAAGCAACATTTGGGGGTGTTGTTTTAAACTGGGTAC
CTATGAAGTGTCTCATCTTGTACGTTGTCTTAGATGGGCATTTGGCAGAT
GTAATAGAGGATCCTAGTGATGACAAGACGACATTGTCAACCAATCCCCC
ACAAGGGAATGAGGACATGTCCTGCAATTCTGAATGGGTTCTCTGATACA
TGTCAGACATGACATAGGCTAGTAGTAGGTTCTAAGCCACGTGTGGACT SEQ ID NO: 7: SP7
CCGAAAATCTGTGGGAAGTCTTGTCCCTCCAATTTTACACCTGTTCAATT
CCCCTGCAGGACAACGCCCACACACCAGGTTAGCCTTTAAGCCTGCCCAG
AAGACTCCCGCCCATCTTCTAGAAAGACTGGAGTTGCAGATCACGAGGGA
AGAGGGGGAAGGGATTCTCCCAGGCCCAGGGCGGTCCTCAGAAGCCAGGA
GGCAGCAGAGAACTCCCAGAAAGGTATTGCAACACTCCCCTCCCCCCTCC
GGAGAAGGGTGCGGCCTTCTCCCCGCCTACTCCACTGCAGCTCCCTT SEQ ID NO: 8. The DNA Sequence of the buffer DNA used in Test 1
GACCTCGAGGGGGGCCCGGTACCCAGCTTTTGTTCCCTTTAGTGAGGGT

TAATTGCGCGCTTGGCGTAATCATGGTCATAGCTGTTTCCTGTGTGAAAT

Table of illustrative sequences DNA sequences of seven spike DNAs mixed to form a testing sample DNA

TGTTATCCGCTCACAATTCCACACAACATACGAGCCGGAAGCATAAAGTG

TAAAGCCTGGGGTGCCTAATGAGTGAGCTAACTCACATTAATTGCGTTGC

GCTCACTGCCCGCTTTCCAGTCGGGAAACCTGTCGTGCCAGCTGCATTAA

TGAATCGGCCAACGCGCGGGGAGAGGCGGTTTGCGTATTGGGCGCTCTTC

CGCTTCCTCGCTCACTGACTCGCTGCGCTCGGTCGTTCGGCTGCGGCGAG

CGGTATCAGCTCACTCAAAGGCGGTAATACGGTTATCCACAGAATCAGGG

GATAACGCAGGAAAGAACATGTGAGCAAAAGGCCAGCAAAAGGCCAGGAA

CCGTAAAAAGGCCGCGTTGCTGGCGTTTTTCCATAGGCTCCGCCCCCCTG

ACGAGCATCACAAAAATCGACGCTCAAGTCAGAGGTGGCGAAACCCGACA

GGACTATAAAGATACCAGGCGTTTCCCCCTGGAAGCTCCCTCGTGCGCTC

TCCTGTTCCGACCCTGCCGCTTACCGGATACCTGTCCGCCTTTCTCCCTT

CGGGAAGCGTGGCGCTTTCTCATAGCTCACGCTGTAGGTATCTCAGTTCG

GTGTAGGTCGTTCGCTCCAAGCTGGGCTGTGTGCACGAACCCCCCGTTCA

GCCCGACCGCTGCGCCTTATCCGGTAACTATCGTCTTGAGTCCAACCCGG

TAAGACACGACTTATCGCCACTGGCAGCAGCCACTGGTAACAGGATTAGC

AGAGCGAGGTATGTAGGCGGTGCTACAGAGTTCTTGAAGTGGTGGCCTAA

CTACGGCTACACTAGAAGGACAGTATTTGGTATCTGCGCTCTGCTGAAGC

CAGTTACCTTCGGAAAAAGAGTTGGTAGCTCTTGATCCGGCAAACAAACC

ACCGCTGGTAGCGGTGGTTTTTTTGTTTGCAAGCAGCAGATTACGCGCAG

AAAAAAAGGATCTCAAGAAGATCCTTTGATCTTTTCTACGGGGTCTGACG

CTCAGTGGAACGAAAACTCACGTTAAGGGATTTTGGTCATGAGATTATCA

AAAAGGATCTTCACCTAGATCCTTTTAAATTAAAAATGAAGTTTTAAATC

AATCTAAAGTATATATGAGTAAACTTGGTCTGACAGTTACCAATGCTTAA

TCAGTGAGGCACCTATCTCAGCGATCTGTCTATTTCGTTCATCCATAGTT

GCCTGACTCCCCGTCGTGTAGATAACTACGATACGGGAGGGCTTACCATC

TGGCCCCAGTGCTGCAATGATACCGCGAGACCCACGCTCACCGGCTCCAG

ATTTATCAGCAATAAACCAGCCAGCCGGAAGGGCCGAGCGCAGAAGTGGT

CCTGCAACTTTATCCGCCTCCATCCAGTCTATTAATTGTTGCCGGGAAGC

TAGAGTAAGTAGTTCGCCAGTTAATAGTTTGCGCAACGTTGTTGCCATTG

CTACAGGCATCGTGGTGTCACGCTCGTCGTTTGGTATGGCTTCATTCAGC

TCCGGTTCCCAACGATCAAGGCGAGTTACATGATCCCCCATGTTGTGCAA

AAAAGCGGTTAGCTCCTTCGGTCCTCCGATCGTTGTCAGAAGTAAGTTGG

CCGCAGTGTTATCACTCATGGTTATGGCAGCACTGCATAATTCTCTTACT

GTCATGCCATCCGTAAGATGCTTTTCTGTGACTGGTGAGTACTCAACCAA

GTCATTCTGAGAATAGTGTATGCGGCGACCGAGTTGCTCTTGCCCGGCGT

CAATACGGGATAATACCGCGCCACATAGCAGAACTTTAAAAGTGCTCATC

ATTGGAAAACGTTCTTCGGGGCGAAAACTCTCAAGGATCTTACCGCTGTT

GAGATCCAGTTCGATGTAACCCACTCGTGCACCCAACTGATCTTCAGCAT

Table of illustrative sequences DNA sequences of seven spike DNAs mixed to form a testing sample DNA

CTTTTACTTTCACCAGCGTTTCTGGGTGAGCAAAAACAGGAAGGCAAAAT

GCCGCAAAAAAGGGAATAAGGGCGACACGGAAATGTTGAATACTCATACT

CTTCCTTTTTCAATATTATTGAAGCATTTATCAGGGTTATTGTCTCATGA

GCGGATACATATTTGAATGTATTTAGAAAAATAAACAAATAGGGGTTCCG

CGCACATTTCCCCGAAAAGTGCCACCTAAATTGTAAGCGTTAATATTTTG

TTAAAATTCGCGTTAAATTTTTGTTAAATCAGCTCATTTTTTAACCAATA

GGCCGAAATCGGCAAAATCCCTTATAAATCAAAAGAATAGACCGAGATAG

GGTTGAGTGTTGTTCCAGTTTGGAACAAGAGTCCACTATTAAAGAACGTG

GACTCCAACGTCAAAGGGCGAAAAACCGTCTATCAGGGCGATGGCCCACT

ACGTGAACCATCACCCTAATCAAGTTTTTTGGGGTCGAGGTGCCGTAAAG

CACTAAATCGGAACCCTAAAGGGAGCCCCCGATTTAGAGCTTGACGGGGA

AAGCCGGCGAACGTGGCGAGAAAGGAAGGGAAGAAAGCGAAAGGAGCGGG

CGCTAGGGCGCTGGCAAGTGTAGCGGTCACGCTGCGCGTAACCACCACAC

CCGCCGCGCTTAATGCGCCGCTACAGGGCGCGTCCCATTCGCCATTCAGG

CTGCGCAACTGTTGGGAAGGGCGATCGGTGCGGGCCTCTTCGCTATTACG

CCAGCTGGCGAAAGGGGATGTGCTGCAAGGCGATTAAGTTGGGTAACGC

CAGGGTTTTCCCAGTCACGACGTTGTAAAACGACGGCCAGTGAGCGCGCG

TAATACGACTCACTATAGGGCGAATTGGAGCTCCACCGCGGTGGCGGCCG

CTCTAGAACTAGTGGATCCCCCGGGCTGCAGGAATTCGATATCAAGCTTA

TCGATACCGTC

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended statements of invention.

The following Statements of the Invention are intended to characterize possible elements of the invention according to the foregoing description given in the specification. Because this application is a provisional application, these statements may become changed upon preparation and filing of the complete application. Such changes are not intended to affect the scope of equivalents according to the claims issuing from the complete application, if such changes occur. According to 35 U. S. C. § 111(b), claims are not required for a provisional application. Consequently, the Statements of the Invention cannot be interpreted to be claims pursuant to 35 U. S. C. § 112.

We claim:

1. A method of treating a sample nucleic acid comprising the steps of: combining the sample nucleic acid with a buffer nucleic acid to produce a total assay nucleic acid, wherein the buffer nucleic acid is distinct from the sample nucleic acid, wherein the mass ratio of the buffer nucleic acid to the sample nucleic acid in the total assay nucleic acid is at least 5, wherein the amount of the sample nucleic acid is equivalent to 100,000× or less coverage of human genome, wherein the method further comprises amplifying the sample nucleic acid and buffer nucleic acid to produce amplified sample nucleic acid and amplified buffer nucleic acid.

2. The method of claim 1, wherein the sample nucleic acid is comprised in a biological sample.

3. The method of claim 1, wherein the amount of sample nucleic acid is 100 pg or less.

4. The method of claim 1, wherein the amount of total assay nucleic acid is 50 pg or greater.

5. The method of claim 1, wherein the buffer nucleic acid contains at least one rare cleavage site.

6. The method of claim 5, wherein the rare cleavage site comprises at least six base pairs and is recognized by a restriction endonuclease.

7. The method of claim 6, wherein the restriction endonuclease is selected from the group consisting of NotI, SfiI, PmeI, PacI, and AscI.

8. The method of claim 1, wherein the sample nucleic acid is from a single cell.

9. The method of claim 1, wherein the method further comprises sequencing the amplified sample nucleic acid and/or amplified buffer nucleic acid.

10. The method of claim 9, wherein the method further comprises sequencing the amplified buffer nucleic acid.

11. The method of claim 1, further comprising the steps of:
   a. treating the amplified sample nucleic acid and amplified buffer nucleic acid with an enzyme, wherein the enzyme cuts each buffer nucleic acid molecule into two or more fragments, and
   b. separating the amplified sample nucleic acid from fragments of amplified buffer nucleic acid.

12. A method of claim 1, wherein the method further comprises ligating one or more adaptors to the buffer nucleic acid and sample nucleic acid before amplification, and wherein the amplification is performed by extending primers binding to one or more adaptors.

13. The method of claim 12, wherein the buffer nucleic acid comprises at least one rare cleavage site per molecule and wherein the method further comprises:

treating the amplified sample nucleic acid and amplified buffer nucleic acid with an enzyme, wherein the enzyme binds to the rare cleavage site and cuts each buffer nucleic acid molecule into two or more fragments, and performing a second round of amplification of the amplified sample nucleic acid and buffer nucleic acid fragments, wherein the second round of amplification is performed by extending primers that bind to the adaptors in the amplified sample nucleic acid.

\* \* \* \* \*

SEQUENCE LISTING

<160> NUMBER OF SEQ ID NOS: 8

<210> SEQ ID NO 1
<211> LENGTH: 439
<212> TYPE: DNA
<213> ORGANISM: Artificial Sequence
<220> FEATURE:
<223> OTHER INFORMATION: Synthetic construct

<400> SEQUENCE: 1

```
gaatattctg tgtcctggga tatcacttcc cgccggaaca gcttgtgatt ggacaaccac      60
agaaccagca ctgtggaggg aagtgtcgc cccgcagcta cacaggcttg tgcctaactc     120
ctgtcttttc ttttttcccag ggaggaagag acagccgctc tggatctccc atggcgagac     180
gctgagagcc ctccccgctc agccttcccg aatcctgccc tcggcttctt aatataactg     240
ccttaaactt ttaattctac ttgcaccgat tagctagtta gagcagaccc tctcttaatc     300
ccgtggagcc gtgatcgcgg tggggccagg cccacggcac cccgactggt aaaactatt     360
cgtcccttt cgtttgaaga ttgagttttc tcggggtctt ctcagccctg acttgttccc     420
cgtgcacctt gttcgactc                                                439
```

<210> SEQ ID NO 2
<211> LENGTH: 504
<212> TYPE: DNA
<213> ORGANISM: Artificial Sequence
<220> FEATURE:
<223> OTHER INFORMATION: Synthetic construct

<400> SEQUENCE: 2

```
tgacttgttc cccgtgcacc ttgttcgact ccggaggttc aggtgcacgg acacccttcc      60
aagttcaccc ctactccatc ctcagacttt tcacggtgag gcacacccct ccagcttccg     120
tgggcactgc ggatagacag gcacaccgcc aaggagccag agagcatggc gcaggggact     180
gtgtggtcca ggcttccttt gttttcttcc ccctaaagag ctttgttttt cctaacagga     240
tcagacagtc ttggagtggc ttatacaacg ggggcttgtg gtatgtgagc acaggctggg     300
cagctgtgag agtccagagt ggggtggccc tggggacact tccaggccag ctatcccctg     360
caccccacca gctgatttcg agcgtggcag agggaaggaa aggggcgagt gggctgggca     420
atggccccaa caggaaacgg ggacttagga gaacacgctg gagatatgtg tggccgccaa     480
atgtcaccat ctctcctcag tggc                                          504
```

<210> SEQ ID NO 3
<211> LENGTH: 497
<212> TYPE: DNA
<213> ORGANISM: Artificial Sequence
<220> FEATURE:
<223> OTHER INFORMATION: Synthetic construct

<400> SEQUENCE: 3

```
aacaggaaac ggggacttag gagaacacgc tggagatatg tgtggccgcc aaatgtcacc      60
atctctcctc agtggctccc cagagctggt gcttttaaga accctgtttc ctctcagagc     120
ccagggagag tccaaggaca tggcgcatct ggaagtggga ctgcaggagt tctctggtgg     180
cctcgtgctg tccctctggc cacttctcat ggtggggtgg tcagcggcag ctcgccatgg     240
cagtgcccat tggtacacac taacctcggt ggaaaaataa ccattccctg cctcctagaa     300
aggactcatt cttagcttta ggggggttcc tgtcactgaa tcgagtcgct gccctggatg     360
cagggctggc ctgggcgacg ctccagggat gaggagctga gaaccccagt ctaataatgt     420
```

```
ccatcgacac ctccttatcc ctctaacgta ctatgtcttt tgatttagca tgccttctgt    480
agaccttcca aagagcc                                                   497
```

<210> SEQ ID NO 4
<211> LENGTH: 492
<212> TYPE: DNA
<213> ORGANISM: Artificial Sequence
<220> FEATURE:
<223> OTHER INFORMATION: Synthetic construct

<400> SEQUENCE: 4

```
aaaaccctcc agattgtccc acgggagtgt tgccctcca gtgtgactga acgaccttgc      60
ccatggcttc gtccagacag cgcagctgca gtatggctgg acagaagcac ctactattct    120
tgaatattga aataaaataa taaacttgca atgatctttg cccaggtgtc tcattttgca    180
cggcagcctg taggcgtgag cccgagtgaa gcacagcctc gtcgcagggt ggagggctct    240
tcctcagggg caccggggttg cttcacggtg cccttgggag aatacctcaa ggggcacgtt    300
gaggaggcca tgcattgata aatcaagaag atggagtaga ggtgatgtgg acagtgacc     360 cacaacacac aaggaaaagg attttcagtc actctgagga cacttttcaa agccattgtc    420
ctaggaaaca ctgcagaaaa gcgggtcacg cgctttatcc acggcggacg gggattaagt    480
gaagcattct tc                                                       492
```

<210> SEQ ID NO 5
<211> LENGTH: 365
<212> TYPE: DNA
<213> ORGANISM: Artificial Sequence
<220> FEATURE:
<223> OTHER INFORMATION: Synthetic construct

<400> SEQUENCE: 5

```
gaacgctgcg cctctgggat ctcacaacgc aagtagctgc tttggaatct tgggggggaaa    60 gtgggcagaa ctgaggtaga ttcgccgggg tgcagtctcc ccttggtaat tggtccttt    120 gtagagggta aagcaacatt tggggtgtt gttttaaact gggtacctat gaagtgtctc    180
atcttgtacg ttgtcttaga tgggcatttg gcagatgtaa tagaggatcc tagtgatgac    240
aagacgacat tgtcaaccaa tcccccacaa gggaatgagg acatgtcctg caattctgaa    300
tgggttctct gatacatgtc agacatgaca taggctagta gtaggttcta agccacgtgt    360
ggact                                                                365
```

<210> SEQ ID NO 6
<211> LENGTH: 449
<212> TYPE: DNA
<213> ORGANISM: Artificial Sequence
<220> FEATURE:
<223> OTHER INFORMATION: Synthetic construct

<400> SEQUENCE: 6

```
gaacgctgcg cctctgggat ctcacaacgc aagtagctgc tttggaatct tgggggggaaa    60 gtgggcagaa ctgaggtaga attcctgcag cccaattccg atcatattca ataaccctta    120
atataacttc gtataatgta tgctatacga agttattagg tccctcgagg ggatcacagt    180
ctccccttgg taattggtcc ttttgtagag ggtaaagcaa catttggggg tgttgtttta    240
aactgggtac ctatgaagtg tctcatcttg tacgttgtct tagatgggca tttgcagat    300 gtaatagagg atcctagtga tgacaagacg acattgtcaa ccaatccccc acaagggaat    360
```

| | |
|---|---:|
| gaggacatgt cctgcaattc tgaatgggtt ctctgataca tgtcagacat gacataggct | 420 |
| agtagtaggt tctaagccac gtgtggact | 449 |

<210> SEQ ID NO 7
<211> LENGTH: 297
<212> TYPE: DNA
<213> ORGANISM: Artificial Sequence
<220> FEATURE:
<223> OTHER INFORMATION: Synthetic construct

<400> SEQUENCE: 7

| | |
|---|---:|
| ccgaaaatct gtgggaagtc ttgtccctcc aattttacac ctgttcaatt cccctgcagg | 60 |
| acaacgccca cacaccaggt tagcctttaa gcctgcccag aagactcccg cccatcttct | 120 |
| agaaagactg gagttgcaga tcacgaggga agagggggaa gggattctcc caggcccagg | 180 |
| gcggtcctca gaagccagga ggcagcagag aactcccaga aaggtattgc aacactcccc | 240 |
| tcccccctcc ggagaagggt gcggccttct ccccgcctac tccactgcag ctccctt | 297 |

<210> SEQ ID NO 8
<211> LENGTH: 2961
<212> TYPE: DNA
<213> ORGANISM: Artificial Sequence
<220> FEATURE:
<223> OTHER INFORMATION: Synthetic construct

<400> SEQUENCE: 8

| | |
|---|---:|
| gacctcgagg gggggcccgg tacccagctt ttgttccctt tagtgagggt taattgcgcg | 60 |
| cttggcgtaa tcatggtcat agctgtttcc tgtgtgaaat tgttatccgc tcacaattcc | 120 |
| acacaacata cgagccggaa gcataaagtg taaagcctgg ggtgcctaat gagtgagcta | 180 |
| actcacatta attgcgttgc gctcactgcc cgctttccag tcgggaaacc tgtcgtgcca | 240 |
| gctgcattaa tgaatcggcc aacgcgcggg gagaggcggt ttgcgtattg ggcgctcttc | 300 |
| cgcttcctcg ctcactgact cgctgcgctc ggtcgttcgg ctgcggcgag cggtatcagc | 360 |
| tcactcaaag gcggtaatac ggttatccac agaatcaggg gataacgcag gaaagaacat | 420 |
| gtgagcaaaa ggccagcaaa aggccaggaa ccgtaaaaag gccgcgttgc tggcgttttt | 480 |
| ccataggctc cgcccccctg acgagcatca caaaaatcga cgctcaagtc agaggtggcg | 540 |
| aaacccgaca ggactataaa gataccaggc gtttccccct ggaagctccc tcgtgcgctc | 600 |
| tcctgttccg accctgccgc ttaccggata cctgtccgcc tttctccctt cgggaagcgt | 660 |
| ggcgctttct catagctcac gctgtaggta tctcagttcg gtgtaggtcg ttcgctccaa | 720 |
| gctgggctgt gtgcacgaac cccccgttca gcccgaccgc tgcgccttat ccggtaacta | 780 |
| tcgtcttgag tccaacccgg taagacacga cttatcgcca ctggcagcag ccactggtaa | 840 |
| caggattagc agagcgaggt atgtaggcgg tgctacagag ttcttgaagt ggtggcctaa | 900 |
| ctacggctac actagaagga cagtatttgg tatctgcgct ctgctgaagc cagttacctt | 960 |
| cggaaaaaga gttggtagct cttgatccgg caaacaaacc accgctggta gcggtggttt | 1020 |
| ttttgtttgc aagcagcaga ttacgcgcag aaaaaaagga tctcaagaag atcctttgat | 1080 |
| cttttctacg gggtctgacg ctcagtggaa cgaaaactca cgttaaggga ttttggtcat | 1140 |
| gagattatca aaaaggatct tcacctagat ccttttaaat taaaaatgaa gttttaaatc | 1200 |
| aatctaaagt atatatgagt aaacttggtc tgacagttac caatgcttaa tcagtgaggc | 1260 |
| acctatctca gcgatctgtc tatttcgttc atccatagtt gcctgactcc ccgtcgtgta | 1320 |
| gataactacg atacgggagg gcttaccatc tggccccagt gctgcaatga taccgcgaga | 1380 |

```
cccacgctca ccggctccag atttatcagc aataaaccag ccagccggaa gggccgagcg    1440
cagaagtggt cctgcaactt tatccgcctc catccagtct attaattgtt gccgggaagc    1500
tagagtaagt agttcgccag ttaatagttt gcgcaacgtt gttgccattg ctacaggcat    1560
cgtggtgtca cgctcgtcgt ttggtatggc ttcattcagc tccggttccc aacgatcaag    1620
gcgagttaca tgatccccca tgttgtgcaa aaaagcggtt agctccttcg gtcctccgat    1680
cgttgtcaga agtaagttgg ccgcagtgtt atcactcatg gttatggcag cactgcataa    1740
ttctcttact gtcatgccat ccgtaagatg ctttctgtg  actggtgagt actcaaccaa    1800
gtcattctga gaatagtgta tgcggcgacc gagttgctct tgcccggcgt caatacggga    1860
taataccgcg ccacatagca gaactttaaa agtgctcatc attggaaaac gttcttcggg    1920
gcgaaaactc tcaaggatct taccgctgtt gagatccagt tcgatgtaac ccactcgtgc    1980
acccaactga tcttcagcat cttttacttt caccagcgtt tctgggtgag caaaaacagg    2040
aaggcaaaat gccgcaaaaa agggaataag ggcgacacgg aaatgttgaa tactcatact    2100 cttcctttt  caatattatt gaagcattta tcagggttat tgtctcatga gcggatacat    2160
atttgaatgt atttagaaaa ataaacaaat aggggttccg cgcacatttc cccgaaaagt    2220
gccacctaaa ttgtaagcgt taatattttg ttaaaattcg cgttaaattt ttgttaaatc    2280
agctcatttt ttaaccaata ggccgaaatc ggcaaaatcc cttataaatc aaaagaatag    2340
accgagatag ggttgagtgt tgttccagtt tggaacaaga gtccactatt aaagaacgtg    2400
gactccaacg tcaaagggcg aaaaaccgtc tatcagggcg atggcccact acgtgaacca    2460
tcaccctaat caagtttttt ggggtcgagg tgccgtaaag cactaaatcg aaccctaaa    2520 gggagccccc gatttagagc ttgacgggga agccggcga  acgtggcgag aaaggaaggg    2580
aagaaagcga aaggagcggg cgctagggcg ctggcaagtg tagcggtcac gctgcgcgta    2640
accaccacac ccgccgcgct taatgcgccg ctacagggcg cgtcccattc gccattcagg    2700
ctgcgcaact gttgggaagg gcgatcggtg cgggcctctt cgctattacg ccagctggcg    2760 aaaggggat  gtgctgcaag gcgattaagt tgggtaacgc cagggttttc ccagtcacga    2820
cgttgtaaaa cgacggccag tgagcgcgcg taatacgact cactataggg cgaattggag    2880
ctccaccgcg gtggcggccg ctctagaact agtggatccc ccgggctgca ggaattcgat    2940
atcaagctta tcgataccgt c                                             2961
```